(12) United States Patent
Van Eyk et al.

(10) Patent No.: US 7,709,193 B2
(45) Date of Patent: May 4, 2010

(54) METHODS AND KITS FOR SEPARATION AND DETECTION OF PROTEINS IN BIOLOGICAL SAMPLES

(75) Inventors: Jennifer E. Van Eyk, Baltimore, MD (US); Jeremy A. C. Simpson, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 687 days.

(21) Appl. No.: 11/138,184

(22) Filed: May 26, 2005

(65) Prior Publication Data

US 2006/0030055 A1 Feb. 9, 2006

Related U.S. Application Data

(63) Continuation of application No. 09/934,297, filed on Aug. 21, 2001, now abandoned.

(60) Provisional application No. 60/226,588, filed on Aug. 21, 2000, provisional application No. 60/308,948, filed on Jul. 30, 2001.

(51) Int. Cl.
*C12Q 1/68* (2006.01)
(52) U.S. Cl. .......................................................... 435/6
(58) Field of Classification Search ................. 435/576, 435/4, 792, 516; 436/518
See application file for complete search history.

(56) References Cited

U.S. PATENT DOCUMENTS

| 5,290,678 A | 3/1994 | Jackowski | 435/7.4 |
| 5,710,008 A * | 1/1998 | Jackowski | 435/7.4 |
| 5,834,220 A | 11/1998 | Wicks et al. | 435/7.92 |
| 6,248,549 B1 | 6/2001 | Van Eyk et al. | 435/15 |
| 7,384,751 B1 | 6/2008 | Van Eyk et al. | 435/7.1 |

FOREIGN PATENT DOCUMENTS

| CA | 2343372 | 7/1998 |
| WO | WO 94/27156 | 11/1994 |
| WO | WO 96/10076 | 4/1996 |
| WO | WO 96/10078 | 4/1996 |
| WO | WO 96/33415 | 10/1996 |

OTHER PUBLICATIONS

U.S. Appl. No. 10/270,838, filed Oct. 11, 2002, Van Eyk et al.
U.S. Appl. No. 09/115,589, filed Jul. 15, 1998, Van Eyk et al.
Database EMBL Accession No. P02643 Jul. 21, 1986 XP-0022745449.
Andres et al., "Contractile proteins in globally "stunned" rabbit myocardium", Basic Res Cardiol 1991 86:219-226.
Bartel et al., "Protein phosphorylation in isolated trabeculae from nonfailing and failing human hearts", Mol Cell Biochem 1996 157 (1-2):171-179.
Bodor et al., "Troponin I Phosphorylation in the Normal and Failing Adult Human Heart", Circulation 1997 96:1495-1500.
Buscemi et al., "p21-Activated Kinase Increases the Calcium Sensitivity of Rat Triton-Skinned Cardiac Muscle Fiber Bundles via a Mechanism Potentially Involving Novel Phosphorylation of Troponin I", Cir Res. 2002 91:509-516.
Collinson et al., "Measurement of cardiac tropoins", Ann Clin Biochem 2001 38:423-449.
Filatov et al., "Troponin: Structure, Properties, and Mechanism of Functioning", Biochemistry 1999 64(9):969-985.
Härtner et al., "Fast and slow isoforms of troponin I and troponin C", Eur. J. Biochem. 1990 188:261-267.
Huang et al., "The Amino Acid Sequences of the Phosphorylated Sites in Troponin-I from Rabbit Skeletal Muscle", FEBS Letters 1974 42(3):249-252.
Jideama et al., "Phosphorylation Specificities of Protein Kinase C Isozymes for Bovine Cardiac Troponin I and Troponin T and Sites within These Proteins and Regulation of Myofilament Properties", J. Biol. Chem. 1996 217(38):23277-23283.
Kaumann et al., "Activation of $\beta_2$-Adrenergic Receptors Hastens Relaxation and Mediates Phosphorylation of Phospholamban, Troponin I, and C-Protein in Ventricular Myocardium From Patients With Terminal Heart Failure", Circulation 1999 99:65-72.
Labugger et al., "Extensive Troponin I and T Modification Detected in Serum From Patients With Acute Myocardial Infarction", Circulation 2000 102:1221-1226.
Li et al., "Phosphorylation and Mutation of Human Cardiac Troponin I Deferentially Destabilize the Interaction of the Functional Regions of Troponin I with Troponin C", Biochemistry 2003 42:14460-14468.
Li et al., "Novel Phosphorylation of Ser 149 in Cardiac Troponin I (cTnI) by PAK Reduces the Affinity of cTnI for Cardiac Troponin C (cTnC)", 46th Annual Meeting of the Biophysical Society 2002 p. 389a 1894-Pos Board #B133.

(Continued)

*Primary Examiner*—Ann Y Lam
(74) *Attorney, Agent, or Firm*—Licata & Tyrrell P.C.

(57) ABSTRACT

Methods and kits are provided for separating a mixture of proteins in a biological sample. Methods for detecting and profiling proteins in biological samples by the separation method and kits are also provided. These methods are particularly useful in assessing damage to cells such as cardiac and skeletal muscle cells and in the early clinical diagnosis of myocardial damage by detection of myofilament proteins in serum of a subject.

33 Claims, 10 Drawing Sheets

OTHER PUBLICATIONS

Lofberg et al., "Myosin Heavy-Chain Fragments and Cardiac Troponins in the Serum in Rhabdomyolysis", Arch Neurol 1995 52:1210-1214.

Matejovicova et al., "Phosphorylation by Protein Kinases A and C of Myofibrillar Proteins in Rabbit Stunned and Non-stunned Myocardium", J Mol Cell Cardiol 1997 29:3189-3202.

McConnell et al., "Troponin I phosphorylation and myofilament calcium sensitivity during decompensated cardiac hypertrophy", Amer. J. Physiol. (Heart Circ Physiol 43) 1998 274:H385-H396.

McDonough et al., "Troponin I Degradation and Covalent Complex Formation Accompanies Myocardial Ischemia/Reperfusion Injury", Circ Res 1999 84:9-20.

Moir et al., "The Phosphorylation Sites of Troponin I From White Skeletal Muscle of the Rabbit", FEBS Letters 1974 42(3):253-256.

Morano et al., "Phosphorylation and Thiophosphorylation by Myosin Light Chain Kinase:Different Effects on Mechanical Properties of Chemically Skinned Ventricular Fibers from the Pig", J Mol Cell Cardiol 1990 22:805-813.

Simpson et al., "Differential Detection of Skeletal Troponin I Isoforms in Serum of a Patient with Rhabdomyolysis:Markers of Muscle Injury?", Clinical Chemistry 2002 48(7):1112-1114.

Solaro et al., "Altered Interactions Among Thin Filament Proteins Modulate Cardiac Function", J Mol Cell Cardiol 1996 28:217-230.

Takeishi et al., "In Vivo Phosphorylation of Cardiac Troponin I by Protein Kinase Cβ2 Decreases Cardiomyocyte Calcium Responsiveness and Contractility in Transgenic Mouse Hearts", J. Clin. Invest. 1998 102:72-78.

Van Eyk et al., "Cardiac Disease-Induced Post-Translational Modifications of Troponin I:Differential Proteolysis, Phosphorylation and Covalent Complex Formation", 44th Annual Meeting of the Biophysical Society Feb. 12-16, 2000 632-POS.

Wilkinson et al., "The Amino Acid Sequence of Troponin I from Rabbit Skeletal Muscle", Biochem. J. 1975 149:493-496.

Westfall et al., "Alterations in Myofibrillar Function and Protein Profiles After Complete Global Ischemia in Rat Hearts", Circulation Research 1992 70:302-313.

Wolff et al., "Myofibrillar Calcium Sensitivity of Isometric Tension Is Increased in Human Dilated Cardiomyopathies", J. Clin. Invest. 1996 98:167-176.

Yuasa et al., "A Novel Interaction of cGMP-dependent Protein Kinase I with Troponin T", J. Biol. Chem. 1999 274(52):37429-37434.

Katrukha et al., "Degradation of cardiac troponin I: implication for reliable immunodetection", *Clinical Chemistry* 1998 44:12 2433-2440.

Marshall T., "Sodium Dodecyl Sulfate Polyacrylamide Gel Electrophoresis of Serum after Protein Denaturation in the Presence or Absence of 2-Mercaptoethanol", *Clin. Chem.* 1984 30/3 475-479.

Marshall et al., "Two-dimensional electrophoresis of human serum proteins following acute myocardial infarction", *Electrophoresis* 1989 10:584-588.

Marshall T., "Electrophoresis of serum isoenzymes and proteins following acute myocardial infarction", *Journal of Chromatography* 1991 569:323-345.

Shi et al., "Degradation of Cardiac Troponin I in Serum Complicates of Cardiac Troponin I Assays", *Clinical Chemistry* 1999 45:7 1018-1025.

Van Eyk et al., "Breakdown and Release of Myofilament Proteins During Ischemia and Ischemia/Reperfusion in Rat Hearts—Identification of Degradation Products and Effects on the pCa-Force Relation", *Cir. Res.* 1998 82:261-271.

Wu et al., "Characterization of cardiac troponin subunit release into serum after acute myocardial infarction and comparison of assays for troponin T and I", *Clinical Chemistry* 1998 44:6 1198-1208.

U.S. Appl. No. 09/419,901, filed Oct. 18, 1999, Van Eyk et al.

Konagaya, M., et al., Increased Serum Myosin Light Chain 3 Level in Neuromuscular Disease. *Muscle & Nerve* 10(5):415-421 (1987).

Larue, C., et al., Immunoradiometric Assay of Myosin Heavy Chain Fragments in Plasma for Investigation of Myocardial Infarction. *Clin. Chem.* 37(1):78-82 (1991).

Ravkilde, J., Creatine Kinase Isoenzyme MB Mass, Cardiac Troponin T, and Myosin Light Chain Isotype 1 as Serological Markers of Myocardial Injury and Their Prognostic Importance in Acute Coronary Syndrome. *Dan. Med. Bull.* 45(1):34-50 (1998).

Takahashi, M., et al., Use of Enzyme Immunoassay for Measurement of Skeletal Tropinin-I Utilizing Isoform-Specific Monoclonal Antibodies. *Clin. Biochem.* 29(4):301-308 (1996).

Lin et al., "Covalent binding of peptides to the N-terminal hydrophobic region of cardiac troponin C has limited effects on function", J. Biol. Chem. 1996 271(1):244-249.

Han et al., "Post-translational chemical modification(s) of proteins", Int. J. Biochem. 1992 24(1):19-28.

Summons to attend oral proceedings pursuant to Rule 115(1) EPC in EP Application No. 01966879 dated Jan. 1, 2009.

Office Action in U.S. Appl. No. 09/419,901 dated Aug. 7, 2008.

* cited by examiner

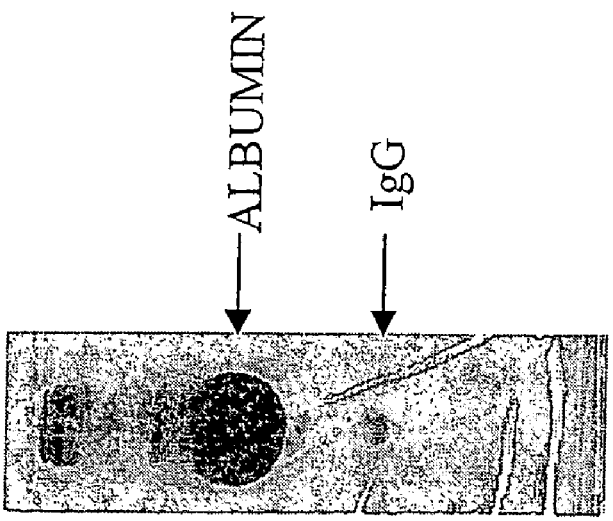
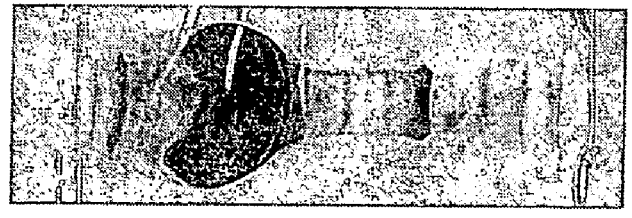

FIGURE 2A
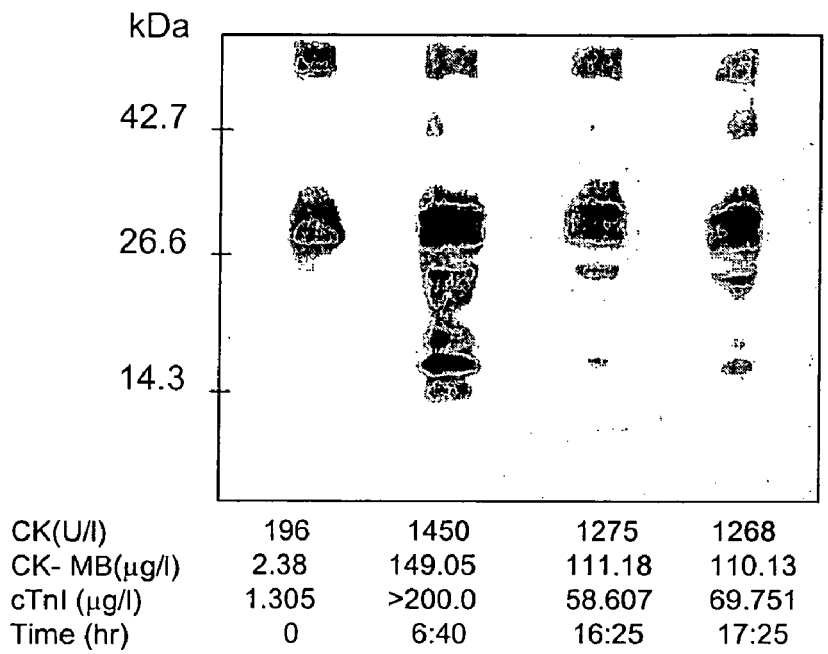
Patient 1: cTnI
| | | | | |
|---|---|---|---|---|
| CK(U/l) | 196 | 1450 | 1275 | 1268 |
| CK-MB(µg/l) | 2.38 | 149.05 | 111.18 | 110.13 |
| cTnI (µg/l) | 1.305 | >200.0 | 58.607 | 69.751 |
| Time (hr) | 0 | 6:40 | 16:25 | 17:25 |
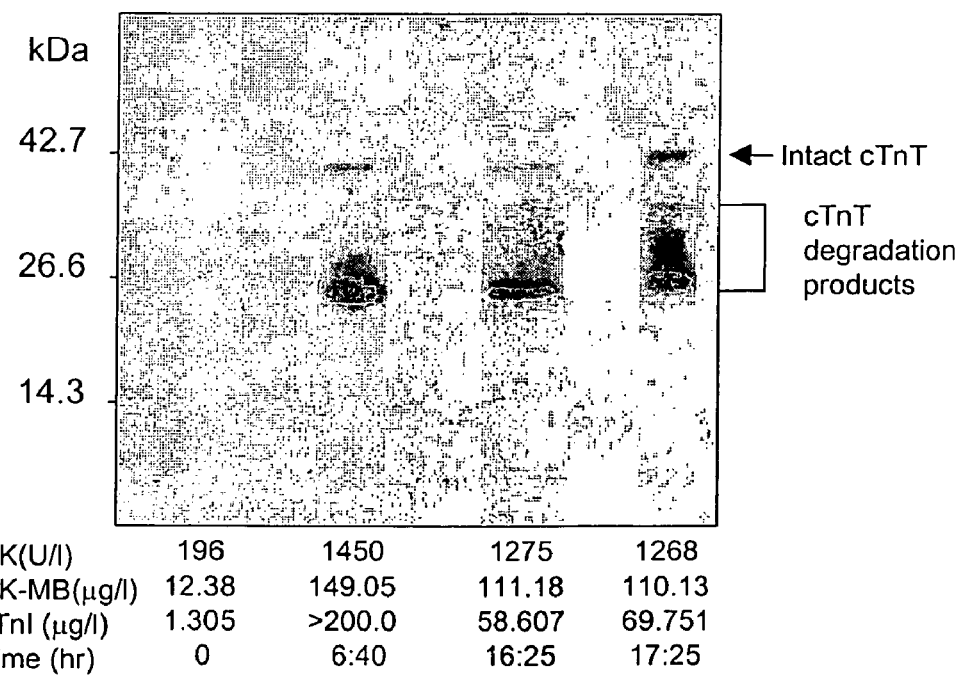
Patient 1: cTnT
| | | | | |
|---|---|---|---|---|
| CK(U/l) | 196 | 1450 | 1275 | 1268 |
| CK-MB(µg/l) | 12.38 | 149.05 | 111.18 | 110.13 |
| cTnI (µg/l) | 1.305 | >200.0 | 58.607 | 69.751 |
| Time (hr) | 0 | 6:40 | 16:25 | 17:25 |

Patient 2: cTnI

Patient 3: cTnI

Patient 4: cTnI

Patient 5: cTnI

Respiratory patient mAb : F-32 mAb : 3I-35

Rhabdomyolysis patient mAb : F-32 mAb : 3I-35

Respiratory patient

Fast skeletal TnI mAb

Time (hr)   0   +8   +17

Slow skeletal TnI mAb    Not detected

Time (hr)   0   +8   +17

Rhabdomyolysis patient

Fast skeletal TnI mAb

Time (hr)   0   +6   +14   +19   +25

Slow skeletal TnI mAb

Time (hr)   0   +6   +14   +19   +25

Rhabdomyolysis patient

Fast skeletal TnI

Prolonged exposure

Slow skeletal TnI

METHODS AND KITS FOR SEPARATION AND DETECTION OF PROTEINS IN BIOLOGICAL SAMPLES

This patent application is a continuation of U.S. patent application Ser. No. 09/934,297 filed Aug. 21, 2001 now abandoned, which claims the benefit of priority to U.S. Provisional Patent Application Ser. No. 60/226,588, filed Aug. 21, 2000 and U.S. Provisional Patent Application Ser. No. 60/308,948, filed Jul. 30, 2001, each of which are herein incorporated by reference in their entirety.

FIELD OF THE INVENTION

The present invention relates to methods and kits for separating a mixture of proteins in a biological sample by mixing the biological sample with a solution which substantially denatures proteins in the biological sample and subjecting the resulting mixture to a protein separation technique. Following separation, proteins of interest are preferably subjected to characterization. As demonstrated herein, the method of the present invention is useful in the development of highly sensitive analytical and diagnostic assays and kits for assessing cellular damage and diagnosing cellular injury in biological samples.

BACKGROUND OF THE INVENTION

It is desirable to be able to separate proteins in biological samples, as well as to subsequently characterize the separated proteins. In a first example, the presence and quantity of particular proteins (i.e., marker proteins) can be used to detect and determine the extent or severity of a disease or other abnormality in an individual. In a second example, the blood of an animal (i.e., a wild type or a transgenic animal) may contain a quantity of a protein of interest (e.g., the product of a transgene). In such a case, it would be convenient to obtain blood from the animal and separate the desired protein or proteins from the other blood proteins. In general, protein separation and characterization can be carried out using any convenient method(s), such as, for example, electrophoresis (e.g., sodium dodecyl sulfate-polyacrylamide gel electrophoresis or SDS-PAGE) and subsequent immunoblotting (e.g., Western blotting).

However, separation/characterization of proteins in serum and plasma is hampered by the presence at high levels of such proteins as albumin and immunoglobulin, which non-specifically bind ("stick") to other proteins. It is known in the art that, when serum is loaded and run on an SDS gel, albumin (blood's primary carrier protein) causes many artifacts, such as smearing, a collapsed lane appearance, and the like (see FIG. 1). The effectiveness of analysis of serum is also limited because such serum proteins often bind to marker proteins, and hence interfere with the migration of the marker proteins on a gel. For an effective analysis, therefore, a marker protein must be separated from any other serum protein that may interfere with its migration on the gel. In enzyme linked immunosorbent assays (ELISAS) and other assays where denaturing is not performed, binding of antibody to a target epitope on the marker protein can be inhibited by the target epitope being hidden by the binding of other proteins to the marker protein. In cases with low serum level of marker protein, such as mild or chronic disease states, where the amount of target epitope is low, the binding by other serum proteins may reduce access to target epitope enough to cause false negative results.

For example, the myofilament proteins cardiac troponin I (cTnI) and cardiac troponin T (cTnT) are biochemical cardiac markers frequently used in the assessment of acute coronary syndrome (ACS) and other myocardial injuries. cTnI and cTnT are not present in the blood of normal, healthy individuals. However, in addition to ACS, elevated marker levels have been found in the blood in cases of congestive heart failure (Missov et al. Circ. 1997 96:2953-2958; Missov and Mair Am. Heart J. 1999 138:95-99), unstable angina (Ottani et al. Am. Heart J. 1999 137:284-291), pulmonary embolism (Giannitsis et al. Circ. 2000 102:211-217), myocarditis (Lauer et al. J. Am. Coll. Cardiol. 1997 30:1354-1359), sepsis and septic shock (ver Elst et al. Clin. Chem. 2000 46:650-657), as well as in patients undergoing percutaneous intervention (Tardiff et al. J. Am. Coll. Cardiol. 1999 33:88-96), cardiac surgery (McDonough et al. Circ. 2001 103:58-64) or implantable cardioverter defibrillator shock application (Schluter et al. Clin. Chem. 2001 47:459-463). cTnI and cTnT in serum have been reported to represent myocardial damage and increased risk of future adverse outcomes (Jaffe et al. Circulation 2000 102:1216-1220). However, problems exist with many of the commercially available detection kits currently in use for these biomarkers.

For example these kits may or may not detect all of the cTnI depending upon the combination of antibodies provided. Further, commercial kits can not differentiate whether or not modified forms of cTnI are present. Nor can these kits identify which forms of cTnI are in the sample. Another problem is that proteins in serum are bound to each other as well as to other proteins which can mask or hide epitopes, thus rendering the proteins undetectable by the antibodies of the kit. Thus, for some patients experiencing an acute myocardial infarction (AMI), the current cTnI kits do not detect all of the intact cTnI and modification products thereof that are released into the serum. In addition, current cTnI kits are not always capable of detecting intact cTnI and modification products thereof in cardiac patients who are not experiencing an AMI, as the commercially available assays appear to have low analytical and diagnostic sensitivity. These patients can be discharged from emergency with a diagnosis of chest pain/not yet diagnosed.

Accordingly, the ability to separate a protein of interest from other proteins in biological samples is important to the development of diagnostic kits with higher analytical and diagnostic sensitivity.

Separation of the protein of interest from other proteins like albumin is also desirable in the case of protein purification from blood, serum or plasma.

Unfortunately, known methods for removing native serum proteins from serum/plasma under native conditions (e.g., non-denaturing, non-reducing conditions, such as immunoprecipitation, acid extraction, gel filtration, ion exchange chromatography) typically lead to substantial loss of the marker protein or proteins, due in large part to the above-mentioned non-specific sticking. In methods where a marker protein or proteins is completely purified from native serum/plasma, analysis of a marker protein level or levels relative to level of other proteins is rendered impossible.

SUMMARY OF THE INVENTION

An object of the present invention is to provide a method of separating a mixture of proteins in a biological sample comprising mixing the biological sample with a solution comprising a sulfhydryl reducing agent, a anionic detergent, and at least one detergent selected from the group consisting of an ionic detergent, a non-ionic detergent and a zwitterionic detergent, at concentrations sufficient to substantially denature proteins in the biological sample, and subjecting the mixture to a separation technique. In a preferred embodiment, following separation, the proteins are further subjected to characterization.

Another object of the present invention is to provide kits for separating a mixture of proteins in a biological sample. Kits of the present invention comprise a solution containing a sulfhydryl reducing agent, an anionic detergent, and at least one detergent selected from the group consisting of another ionic detergent, a non-ionic detergent and a zwitterionic detergent, and instructions for separating proteins in said biological sample. In a preferred embodiment, kits of the present invention further comprise a means for characterization of a separated protein or proteins.

Another object of the present invention is to provide methods for producing a profile of proteins in a biological sample which comprises mixing the biological sample with a solution comprising a sulfhydryl reducing agent, an anionic detergent, and at least one detergent selected from the group consisting of an ionic detergent, a non-ionic detergent and a zwitterionic detergent, at concentrations sufficient to substantially denature proteins in the biological sample, and subjecting the mixture to separation and characterization so as to produce a profile of proteins in said biological sample.

Another object of the present invention is to provide kits for producing a profile of proteins in a biological sample. Kits of the present invention comprise a solution containing a sulfhydryl reducing agent, an anionic detergent, and at least one detergent selected from the group consisting of another ionic detergent, a non-ionic detergent and a zwitterionic detergent, and instructions for separating proteins in said biological sample. Kits of the present invention further comprise a means for characterization of the separated proteins so that a profile of proteins in the biological sample can be generated.

As demonstrated herein, the methods and kits of the present invention are particularly useful in assessing cell damage in a subject. In one embodiment, a biological sample such as serum containing a mixture of proteins from a subject is mixed with a solution comprising a sulfhydryl reducing agent, an anionic detergent, and at least one detergent selected from the group consisting of an ionic detergent, a non-ionic detergent and a zwitterionic detergent, at concentrations sufficient to substantially denature proteins in the biological sample. The mixture is then subjected to separation and the separated proteins are characterized so that proteins indicative of damage to the cell or cells in the subject can be detected.

For example, using the methods and kits of the present invention, a profile can now be generated from a serum sample of a subject which is indicative of a distinct cardiovascular condition or elapsed time after onset of an AMI or severity of an infarct or reinfarction. The methods and kits of the present invention can also be used for detection of a single myofilament protein in a biological sample such as serum for early clinical assessment, ongoing monitoring of chronic conditions and/or diagnosis of myocardial damage in subjects, particularly subjects with non-diagnostic electrocardiograms and/or where routine clinical testing shows non-significant elevations of biochemical cardiac markers. In addition, these methods and kits can be used to monitor the state of the myocardium in a subject by monitoring myofilament protein levels, preferably myofilament protein modifications, in serum.

Alternatively, the methods and kits can be used to detect and monitor skeletal muscle damage in a biological sample of a subject. For example, using the present invention it was demonstrated that myofilament proteins were detectable in serum of a subject following skeletal muscle damage, e.g. respiratory muscle injuries. Thus, damage to skeletal muscle, as well as healing and regeneration of the skeletal muscle following muscle damage can be monitored. In one embodiment, the ratio of two different isoforms of a skeletal myofilament protein such as TnI or TnT, are monitored to assess the severity of a disease involving skeletal muscle. For example, in this embodiment the ratio of the fast form of TnI versus the slow form of TnI can be measured to diagnosis and monitor the state and type of skeletal muscle damage in a subject.

The methods and kits can also be used to differentiate between various isoforms of a protein such as between a cardiac and skeletal myofilament protein.

In a preferred embodiment of the present invention, the method is performed on serum samples and the characterization following separation is performed by western-blot. This preferred method is referred to herein as Western Blot-Direct Serum Analysis or WB-DSA.

BRIEF DESCRIPTION OF THE FIGURES

FIG. 1 provides a comparison of a human serum sample separated in accordance with the method of the present invention prior to loading (lane A) and the same human serum sample treated with SDS as the only detergent in the loading buffer (lane B). Both samples were subjected to SDS-PAGE and stained with Coomassie blue.

FIG. 9 provides a western blot of serum analyzed by WB-DSA of serial time points (initial sample time point. designated time zero) of a patient with rhabdomyolysis. As shown in FIG. 9B, some modification products were present at specific time points during the progression of the disease (proteolytic fragment designated by arrow). Changes in the total amounts of the protein, as well as changes in the ratio of the fast and slow isoforms, were also detected.

DETAILED DESCRIPTION OF THE INVENTION

Figure 2B:
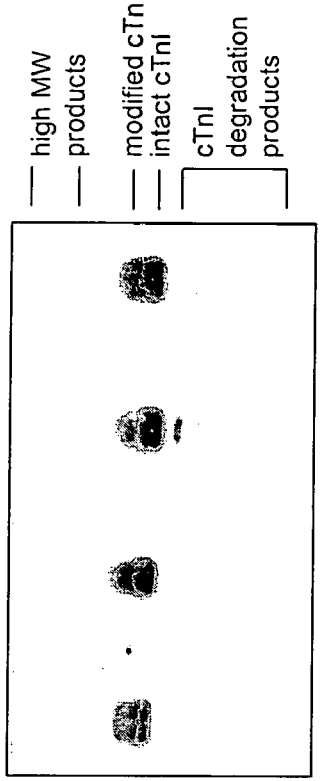
FIG. 2 shows a spectrum of cTnI and cTnT modifications found in AMI patient serum. cTnI and its modification products in AMI patient serum were detected by the anti-cTnI mAb 8I-7. WB-DSA of serial serum samples obtained from 5 patients is shown in panels a, b, c, d and e. The samples from patient 1 were also probed for cTnT and its degradation products (cTnT Degn) with an anti-cTnT pAb (panel a, lower). The time course begins (t=0) when the first blood sample was drawn after patient arrival at the hospital emergency room and subsequent times at which blood samples were drawn are listed. The corresponding levels of creatinine kinase, the isoenzyme of creatine kinase (CKMB) and cTnI at each of these times are also indicated. The relative positions of molecular weight markers are indicated to the left. NSQ=non-sufficient quantity of sample. Exposure times of these western blots were optimized for better visual interpretation of the results for each individual patient. Direct comparison of the intensity of appearing bands is therefore inappropriate between patients.
Figure 2C:
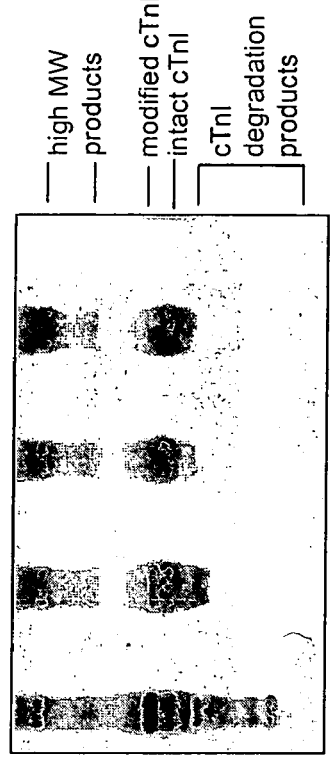
Figure 2D:
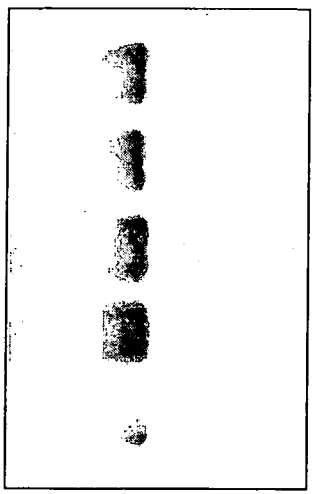
Figure 2E:
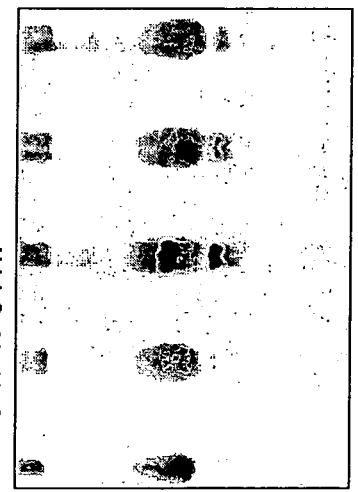

The present invention provides methods for separating a mixture of proteins in a biological sample by mixing the biological sample with a solution which substantially denatures proteins in the biological sample and subjecting the resulting mixture to a protein separation technique. These methods are useful in the detection of single proteins in a biological sample as well as in profiling a number of proteins in the sample.

For purposes of the present invention, by "biological sample" it is meant to include, but is not limited to, serum, plasma, urine, milk, lymph, amniotic fluid, semen and cerebrospinal fluid. In a preferred embodiment, the biological sample is serum.

The present invention is based, at least in part, on the discovery that the confounding effect of other serum proteins binding to protein(s) of interest can be overcome by subjecting the serum to strong denaturing and sulfhydryl reducing conditions. Accordingly, the present invention provides methods for separating proteins of a biological sample such as serum by mixing the serum with a solution comprising a sulfhydryl reducing agent, an anionic detergent (preferably sodium dodecyl sulfate, SDS), and at least one detergent selected from the group consisting of an ionic detergent, a non-ionic detergent and a zwitterionic detergent. The solution comprises the sulfhydryl reducing agent and the detergents at concentrations sufficient to substantially denature proteins in the mixture. The mixture of serum and solution comprising the thus-denatured proteins is then subjected to separation, and optionally further characterization.

Preferably, the serum and solution mixture is heated after the mixing step and prior to the separation step, and the concentrations of the sulfhydryl reducing agent and the selected detergents in the solution are sufficient to substantially denature proteins in the serum and solution mixture when heated. Still more preferably, the serum and solution mixture is boiled, and the concentrations of the sulfhydryl reducing agent and the selected detergents are sufficient to substantially denature proteins when the serum and solution mixture is boiled.

Separation may be performed using any convenient means. In a preferred embodiment, SDS-PAGE is used. However, other separation techniques including, but not limited to, capillary electrophoresis, fast system mini-gels, affinity chromatography, ion exchange chromatography and reverse phase chromatography (conventional or high performance) can also be used. However, if gel filtration, capillary electrophoresis or some other separation technique is employed, care must be taken to maintain the proteins of the mixture in a state where they do not become complexed with undesirable proteins such as albumin. That is, the proteins should preferably be maintained in a substantially denatured state. This may be achieved by employing buffer containing detergent and/or denaturing and/or reducing agents. Subsequently, the protein of interest, having been separated from other (sticky) proteins present in the serum starting material, may be renatured, e.g., by dialyzing into buffer that does not contain a denaturing agent.

The solution used in the separation method of the present invention comprises a sulfhydryl reducing agent, an anionic detergent, and at least one of an ionic detergent, a non-ionic detergent or a zwitterionic detergent. In a preferred embodiment, the solution comprises a sulfhydryl reducing agent, an anionic detergent, a non-ionic detergent and a zwitterionic detergent. In some embodiments, the solution further comprises urea or thiourea.

Concentrations of the components of the solution must be sufficient to achieve substantial, or complete denaturation. For example, 1 to 2% SDS, in conjunction with a reducing agent such as BME, is commonly employed in the art in SDS-PAGE loading buffer. However, these concentrations are insufficient to completely denature serum proteins such as albumin so that proteins in the sample are well resolved by SDS-PAGE. Rather, the proteins appear as a huge smear on the resulting gel (see FIG. 1). Further, simply increasing the SDS concentration of standard loading buffer to 4% fails to produce any improvement in resolution. The addition of one or more detergents as set forth in the present invention, however, provides a substantial increase in resolution of proteins.

As used herein, the term "protein" is intended to mean any protein, polypeptide, peptide, or fragment thereof, as well as protein-modification products, such as, for example, phosphorylated proteins, glycosylated proteins, radio-iodinated proteins, and the like. Further, by use of the term protein it is meant to be inclusive of one or more proteins. By protein it is also meant to be inclusive of post-translationally modified proteins including not only phosphorylation of amino acid residues, but also of other chemical adducts. Chemical adducts known in the art relating to post-translational modification of proteins which can be separated using the present invention include, but are not limited to, phosphorylation, glycosylation, myristylation, phenylation, acetylation, nitrosylation, s-glutathiolation, amidation, biotinylation, c-mannosylation, flavinylation, farnesylation, formylation, geranyl-geranylation, hydroxylation, lipoylation, methylation, palmitoylation, sulphation, gamma-carboxyglutamic acids, N-acyl diglyceride (tripalmitate), O-GlcNAc, pyridoxal phosphate, phospho-pantetheine, and pyrrolidone carboxylic acid. Preferred chemical adducts are phosphorylation, glycosylation, myristylation, phenylation, acetylation, nitrosylation, and sulphation. By "modifications", it is meant to be inclusive of both naturally occurring modifications and artificially induced modifications.

As used herein, the term "substantially denatured" is intended to mean that at least 90% of the protein or proteins in the biological sample is denatured.

As used herein, the term "characterizing" or "characterization" is intended to encompass detecting, identifying, profiling, and quantifying one or more proteins in a biological sample, by any means known in the art. The presence or absence of a chosen protein, or its level relative to the level of another protein or proteins, or a change in the level of a protein over time, may be determined. Accordingly, the invention provides profiles that are characteristic of certain physiological conditions, wherein the levels of one, two, three or more proteins or protein-modification products present in a biological sample such as serum or plasma are determined relative to each other. Any convenient technique for characterization may be employed. In a preferred embodiment, gel electrophoresis following by further analysis by immunoblotting, preferably Western blotting is used. This preferred method of the present invention is referred to herein as Western Blot-Direct Serum Analysis or WB-DSA.

In general, Western blotting (WB) is a three-step procedure commonly used to separate a mixture of proteins and then identify a protein of interest. The first step requires separating a protein mixture by electrophoresis on an SDS-polyacrylamide gel (SDS-PAGE). Next, the resolved proteins in the gel are transferred (by electroblotting) to a paper-thin nitrocellulose membrane which binds most proteins. In the final step, the protein or proteins of interest is detected on the protein-studded membrane. In a preferred embodiment, the protein-studded membrane is soaked in a solution of antibodies that are specific for the protein or proteins of interest. In one embodiment, antibodies in this solution can be labeled for easy detection of protein-bound antibodies. In another embodiment, the protein-bound antibodies can be detected using a second antibody that is specific for the first. This second antibody may be bound to a fluorescing enzyme that is detected using radiographic film or a calorimetrically detectable enzyme such as horse radish peroxidase or alkaline phosphatase. Modified proteins may also be detected by P32 labeling or lectin binding to carbohydratess. More recently, a technique has been developed referred to as UNIBLOT (Pierce Chemicals) which allows the western blot to be performed directly on the gel without the need for transfer of the resolved proteins to a nitrocellulose or PVDF membrane.

The WB-DSA procedure used in the present invention overcomes problems limiting the application of SDS-PAGE to serum. Specifically, large quantities of albumin and IgG in serum hamper migration within a polyacrylamide gel and limit the sample volume that can be applied to the gel. These large quantities of proteins overwhelm the small amounts of proteins which may be present in early clinical diagnosis of diseases such as myocardial damage. Using the method of present invention to separate proteins of a biological sample, however, only 1 to 3 μl, preferably 2 μl of serum is required for reliable detection of proteins such as myofilament proteins in serum.

When SDS-PAGE is used as the separation technique in the present invention, it is preferred that the gel electrophoresis be performed under denaturing and reducing conditions. For example, in one embodiment, a sample buffer containing 0.33% SDS, 0.33% CHAPS, 0.33% NP-40, 0.1 M DTT, 4 M urea, and 50 mM Tris-HCl, pH 6.8 in 50% glycerol is used. Serum is diluted, preferably about 12.5 times, in the sample buffer to prevent precipitation of serum proteins during boiling. Diluted samples are then preferably boiled for 10 minutes to assure separation of the myofilament proteins from serum proteins and to break-up binary and ternary complexes. Approximately 12.5 to 37.5 μl, preferably 25 μl (equivalent to 2 μl of neat serum) is then loaded on 10% to 15% gradient gels, preferably with dimensions of approximately 10-14 cm×8-14 cm×0.75-1.5 mm. The gels are run at 100-150 V for 1.5 to 5 hours. After gel electrophoresis, proteins are transferred onto nitrocellulose (45 Micron, Micton Separation Inc., Westborough, Mass.) in 10 mM CHAPS, pH 11.0, for 30 minutes to 19 hours at 25 to 100 V and 4° C. Alternatively, PVDF membranes such as Immobilon-P (Millipore) can be used and the transfer performed in a buffer containing 25 mM Tris-HCl, 192 mM glycine, and 20% methanol for 1.5 hours at 200 mA. Thereafter, membranes are blocked overnight at 4° C. in 10% blocking reagent (Boehringer Mannheim, Mannheim, Germany).

The present invention also relates to kits for separating a mixture of proteins in a biological sample. Such kits are useful in the detection of one or more proteins in a biological sample and in the profiling a more than one protein in a biological sample. In simplest form, kits of the present invention comprise a solution containing a sulfhydryl reducing agent, an anionic detergent, and at least one detergent selected from the group consisting of an ionic detergent, a non-ionic detergent and a zwitterionic detergent, and instructions for separating proteins in the biological sample. Kits of the present invention preferably further comprise a means for detecting one or more proteins in the sample or a means for profiling various proteins in the sample.

Examples of suitable sulfhydryl reducing agent which can be used in the solution of the methods and kits of the present invention include, but are not limited to, dithiothreitol (DTT), dithioerythritol (DTE) and β-mercaptoethanol (BME). However, as will be understood by one of skill in the art upon reading this disclosure, other sulfhydryl reducing agents known in the art can also be used in the solution.

A suitable zwitterionic detergent that can be used in the methods and kits of the present invention is 3[(3-chlolamidopropyl)dimethyl-ammonio]-1-propane sulfonate (CHAPS), and a suitable non-ionic detergent is ethylphenolpoly(ethylene-glycolether)$_n$ (Igepal CA-630, formerly known as Nonidet P-40 or NP-40). Additional suitable zwitterionic detergents include, without limitation, N-alkyl-N,N-dimethylammonio-1-propanesulfonates. Additional suitable non-ionic detergents include, without limitation, Triton X-100, Triton X-114, n-octyl-glucoside, digitonin, Tween, Tween 20, Tween 80, and saponin. When a combination of two or more detergents is employed, the detergents can be combined in equal portions, or the portions can be optimized for a specific application through routine experimentation. Similarly, when a combination of three detergents is employed, the detergents can be combined in equal portions, or the portions can be optimized for a specific application through routine experimentation.

For serum samples, a preferred solution comprises about 70 mM SDS and about 100 mM DTT. More preferred is a solution comprising the components as set forth in Table 1.

TABLE 1

Serum Protein Separating Solution

| Component | Preferred Concentration Range for 12.5X dilution |
|---|---|
| SDS | about 5 mM to about 150 mM; preferably about 25 mM to about 100 mM |
| CHAPS | about 5 mM to about 50 mM; preferably about 5 mM to about 25 mM |
| Igepal CA-630 | about 0.2% to about 4%; preferably about 1% to about 2% |
| DTT | about 5 mM to about 150 mM; preferably about 50 mM to about 120 mM |
| Urea | about 0.2 M to about 8 M; preferably about 1 M to about 2 M |
| buffer solution | low salt, inorganic, neutral pH; e.g., 50 mM Tris-HCl, pH 6.8 |

Concentrations as set forth in Table 1 are those of the final solution.

As can be seen from FIG. 1 (lane A), which shows a Coomassie blue-stained gel of human serum prepared for SDS-PAGE according to a preferred embodiment of the invention (i.e., with SDS, CHAPS, Igepal CA-630, urea, and DTT), there is distinct separation (resolution) of the proteins (compare with FIG. 1 (lane B), described above).

The concentrations of components in the solution as set forth in Table 1 have been optimized for serum samples. Other biological samples such as plasma, urine, milk, lymph, amniotic fluid, semen and cerebrospinal fluid contain different amounts of proteins than serum. Accordingly, protocols employed in separation techniques exemplified herein may require minor modification to take this into account; this may be as simple as decreasing or increasing the amount of starting material, or the like. It is believed that the methods and kits of the present invention will be particularly applicable to biological samples such as milk which contains carrier proteins such as casein, which may non-specifically bind to a protein(s) of interest (e.g., marker protein(s), the product of a transgene which is secreted into milk). Inasmuch as the methods of the invention apply to milk and other complex mixtures of proteins, they may be employed for separation and characterization of same.

It is widely accepted that the presence of cardiac troponin I or T (cTnI or cTnT) in serum indicates myocardial damage, thus making them specific biochemical markers for acute myocardial infarction (AMI) (Chapelle, J. P. Clin Chem Lab Med. 1999 37:11-20; Wu, A. H. Coronary Artery Dis. 1999 10:69-74; and Antman et al. N Engl J Med. 1996 335:1342-1349. Despite widespread use of cTnI and cTnT detection as diagnostic tools in acute coronary syndromes (ACS), however, problems arise from variations in the sensitivity, selectivity and specificity among various commercially available diagnostic TnI immunoassay kits (Katus et al. Circulation 1991 83:902-912; Hamm et al. N Engl J Med. 1992;327:146-150). These differences are due to (I) the lack of mass standardization (Antman et al. N Engl J Med. 1996 335:1342-1349; Katus et al. Circulation 1991 83:902-912; Hamm et al. N Engl J Med. 1992 327:146-150; Stromme et al. Scand J Clin Lab Invest. 1998 58:693-699; Katrukha et al. Scand J Clin Lab Invest Suppl. 1999 230:124-127; Tate et al. Clin Chim Acta. 1999 284:141-149; Newman et al. Clin Chem. 1999 45(6 Pt 1):822-828; Shi et al. Clin Chem. 1999 45:1018-1025) (ii) the presence of post-translationally modified cTnI in serum and (iii) variations in antibody cross-reactivities to the various detectable forms of cTnI (Shi et al. Clin Chem. 1999 45:1018-1025; Wu et al. Clin Chem. 1998 44(6 Pt 1):1198-1208).

Based on previous findings, it has been proposed that only a small amount of free intact cTnI is detectable in blood, with the predominant form being a cTnI-cTnC complex (Wu et al. Clin Chem. 1998 44(6 Pt 1):1198-1208; Giuliani et al. Clin Chem. 1999;45:213-222; Morjana, N. A. Biotechnol Appl Biochem. 1998;28(Pt 2):105-111). However, post-translational modifications, including selective degradation, covalent complex formation, and phosphorylation of cTnI, have been demonstrated in the myocardium of ischemic-reperfused rat hearts (Gao et al. Circ Res. 1997 80:393-399; McDonough et al. Circ Res. 1999 Jan 8-22 84:9-20; Van Eyk et al. Circ Res. 1998;82:261-271) and human post-ischaemic myocardium (Murphy et al. Science 2000 287:488-491; and McDonough et al. Circulation. 1999 100:I-767:abstract 4047). In fact, these modification products, and not intact cTnI, are preferentially detected in the effluent from severely ischaemic rat hearts (McDonough et al. Circ Res. Jan. 8-22, 1999 84:9-20). In human myocardium, cTnI proteolysis is even more extensive and complex, in part due to the heterogeneity of disease states present in a given patient population (McDonough et al. Circulation 1999 100:I-767; abstract 4047). Similar considerations apply to cTnT, the detection of which has been proposed to be equivalent or superior to cTnI as a biochemical marker for myocardial ischaemia (Apple, F. S. Clin Chim Acta. 1999 284:151-159). Nevertheless, the significance of the necrotic release of these modified products has not been investigated, in spite of their possible clinical importance as a correlate to the subsequent progression of ischaemic heart disease.

Figure 5:
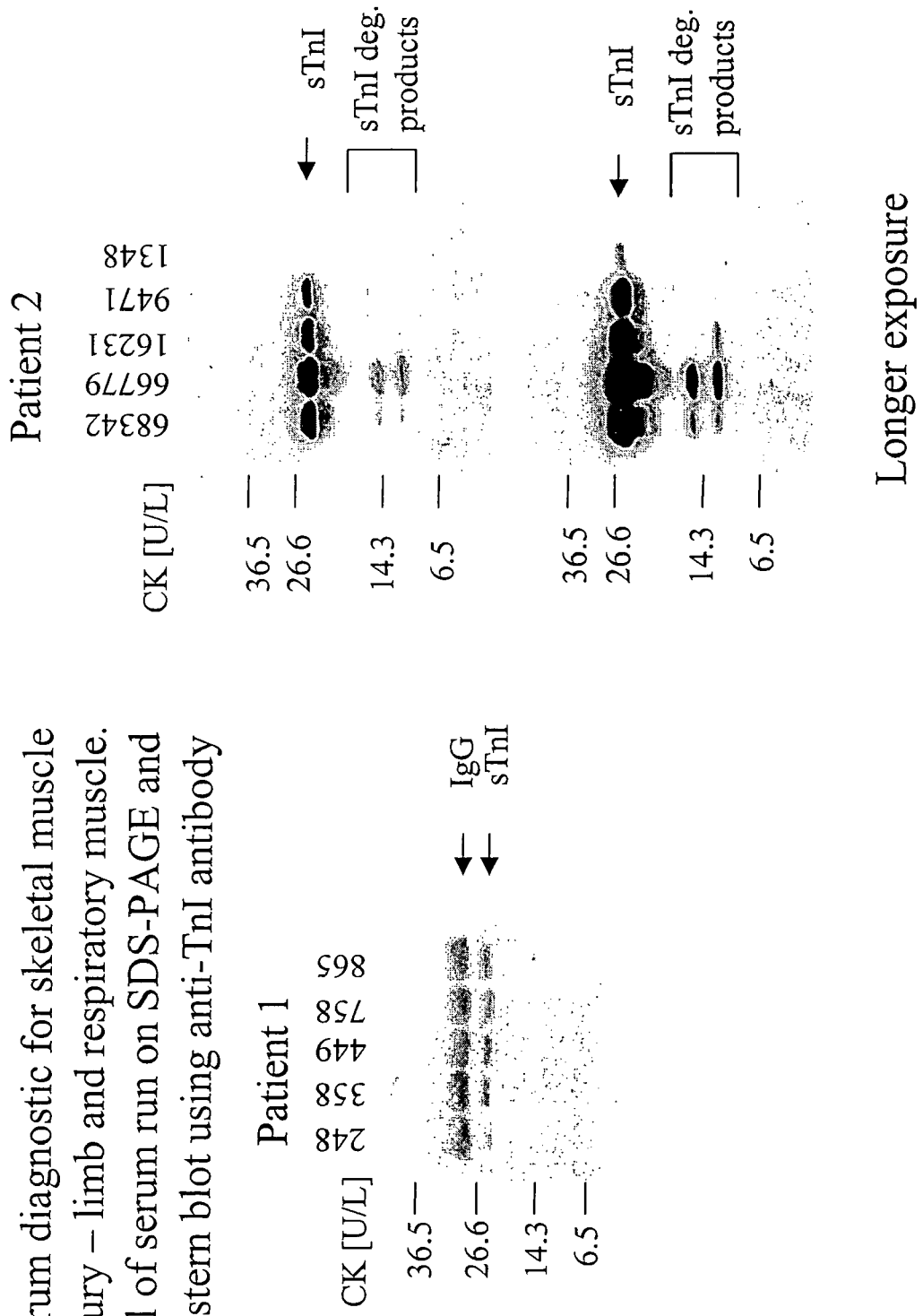
FIG. 5 shows human serum from a patient with respiratory muscle (diaphragm) injury (Patient 1) and human serum from a patient with a limb injury (Patient 2). Samples were pretreated according to separation method of the present invention, subjected to SDS-PAGE and visualized by western blotting with anti-skeletal TnI antibody.

Using the method of the present invention, it is now possible to characterize cellular proteins, as well as their modification products, in a biological sample to assess injury to the cells. For example, the method of the present invention has been used to characterize myofilament proteins as well as their modification products in a serum sample to assess muscle damage in a subject. In this method, a serum sample from the subject is first obtained. The serum sample is then mixed with a solution comprising a sulfhydryl reducing agent, an anionic detergent, and at least one detergent selected from the group consisting of an ionic detergent, a non-ionic detergent and a zwitterionic detergent, at concentrations sufficient to substantially denature albumin in the mixture. This mixture of serum and solution is then separated, and the separated proteins are characterized. Myofilament proteins which can be characterized in serum include, but are not limited to, troponin I, troponin T, myosin light chain 1, myosin light chain 2, actin, actinin, desmin, caldesmin, titin, protein C and calponin, as well as modification products thereof. Damage may be assessed in both cardiac and skeletal muscle as evidenced by FIGS. 2, 3 and 5, and the characterized proteins (profile) provide an indication of damage or potential damage, the disease or condition causing the damage, and the state or condition of the subject with the disease or condition.

For example, progression of cardiac TnI and cardiac TnT modification products present in the serum of AMI patients was monitored using the method of the present invention. In these experiments, serum from 12 patients diagnosed with AMI was first separated using the method of the present invention and then subjected to Western Blot to characterize the proteins. This procedure is referred to hereinafter as Western Blot-Direct Serum Analysis or WB-DSA.

FIG. 2 provides western blots from serum for 5 representative AMI patients subjected to WB-DSA. In addition to intact cTnI, as many as 8 truncated degradation products and 3 products of higher molecular weight were observed. The number and extent of cTnI modifications in each patient changed throughout the time course following infarction. This profile of the visually detectable cTnI modification products, as well as their intensity, as indicated by WB-DSA, corresponded with the time profiles of serum CK, CKMB and cTnI, as determined by CX7 and Immunol.

Figure 3:
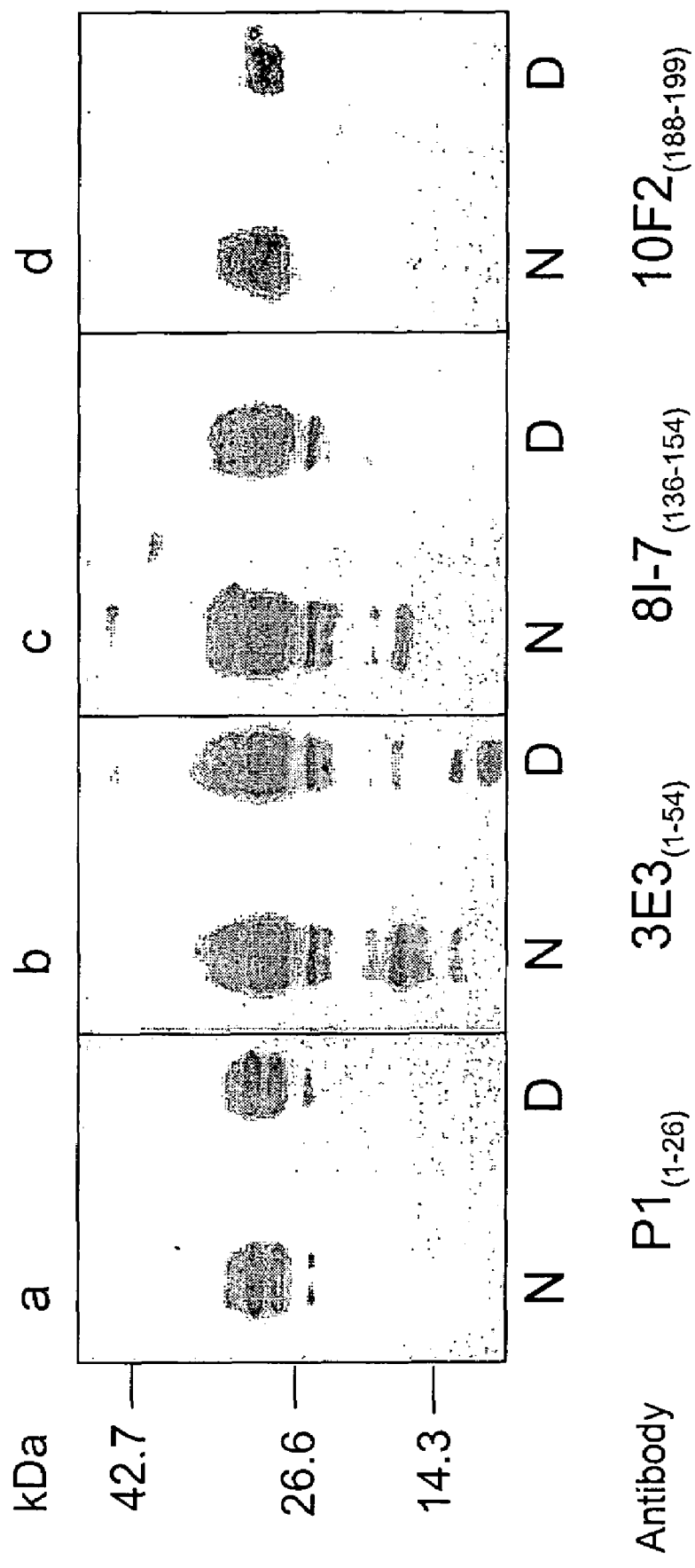
FIG. 3 shows the characterization of cTnI modification products present in AMI patient serum. WB-DSA using 4 anti-cTnI antibodies to different epitopes on cTnI (blots a-d) are shown for native patient serum (N) and for native serum following dephosphorylation (D). Antibodies used are listed beneath their corresponding blots with their epitope in subscript. The relative positions of molecular weight markers are indicated to the left.

Western blot analysis of serum samples from Patient 1, using an anti-cTnT pAb, showed massive degradation of intact cTnT to a single truncated product with a molecular weight of about 26 kDa (FIG. 2a). In addition, 2 further products appeared in the final sample. Like cTnI, the amount of cTnT detectable in patients' serum changed over time following an AMI. This profile also corresponded to the time profiles of serum CK, CKMB and cTnI. It is interesting to note that for this particular patient, cTnI was detected before cTnT.

Dephosphorylation of serum verified that some of the cTnI (intact as well as modified products) found in patients' serum is phosphorylated. While some antibodies (FIG. 3b-d) seemed to change their immunoreactivity towards cTnI due to dephosphorylation of serum, others (FIG. 3a) were not affected. Phosphorylated cTnI has not been shown previously in serum of patients with AMI. Serum from an AMI patient incubated in dephosphorylation buffer in the absence of alkaline phosphatase served as a negative control for the dephosphorylation experiment and showed no difference in the cTnI pattern when compared with native conditions.

The cTnI fragments all arose from C-terminal truncations, as shown by the lack of immunoreactivity to the C-terminal anti-cTnI antibody 10F2 (FIG. 3d). In addition, it was clear that degradation products below a molecular weight of 22 kDa resulted from both N— and C-terminal truncations, as evidenced by the lack of interaction with the N-terminal anti-cTnI antibody P1 (FIG. 3a).

Figure 4:
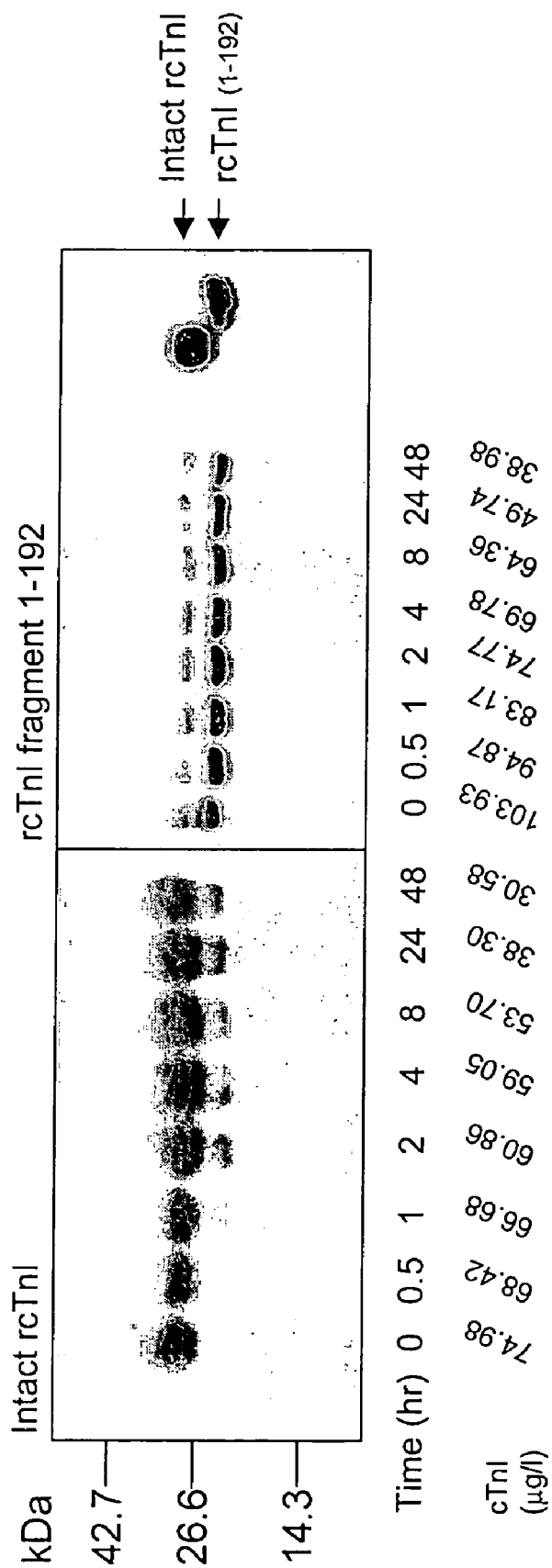
FIG. 4 shows results from a stability study with human recombinant cTnI (rcTnI). The stability of human rcTnI in normal serum, incubated at 37° C. for up to 48 hours, was determined by WB-DSA using anti-cTnI mAb 8I-7. Cardiac TnI levels, determined by IMMUNO1 for each time point, are listed beneath the blots. The relative positions of molecular weight markers are indicated to the left.

Determination of whether protein modifications, detected in serum, occurred within the myocardium prior to, or following release from the myocardium, was addressed by addition of human rcTnI, $rcTnI_{1-192}$ or rcTnT to normal serum followed by incubation at 37° C. for up to 48 hours (FIG. 4). The Immunol results demonstrated a dramatic decline in detectable cTnI for both the intact form and the 1-192 fragment (FIG. 4). Based on WB-DSA, rcTnI underwent degradation within 30 minutes in serum, forming a fragment that migrated in a gel at the same position as $rcTnI_{1-192}$ (FIG. 4). No additional cleavage products were detected, and no further substantial degradation was observed. A reduction of total rcTnI after 2 hours (which may explain the dramatic decline in detectable cTnI by Immunol) was observed. This is supported by control experiments in which a 5-fold excess of spiked rcTnI, relative to the amount resolved in FIG. 4, showed the same discrete proteolysis.

Degradation of $rcTnI_{1-192}$ (FIG. 4) occurred to a lesser extent than that observed for rcTnI and, again, no reduction of total protein was detected over a period of 48 hours. In contrast, human rcTnT did not degrade in normal serum (data not shown). Freeze/thawing of both normal serum containing rcTnI and rcTnT as well as patients' serum also produced no change in the pattern of protein degradation detectable by WB-DSA.

Thus, as demonstrated by these experiments, the method of the present invention allows for the direct detection of cTnI and cTnT in serum from patients with diagnosed AMI. As also demonstrated by these experiments, the method of the present invention provides means to obtain characteristic profiles of proteins such as troponin modification products or a distinct pattern of products over time, which can indicate a distinct cardiovascular condition or a specific elapsed time after onset of an AMI or potentially the severity of an infarct or reinfarction. Thus, this invention provides a new immunological diagnostic tool for measuring the variety of forms of troponin in a patient's blood which is useful not only to detect myocardial damage, but also to provide more information about the condition of the diseased myocardium and its viability. This provides for therapeutic applications, and a more differentiated risk stratification of patients with acute coronary syndromes.

Figure 9A:
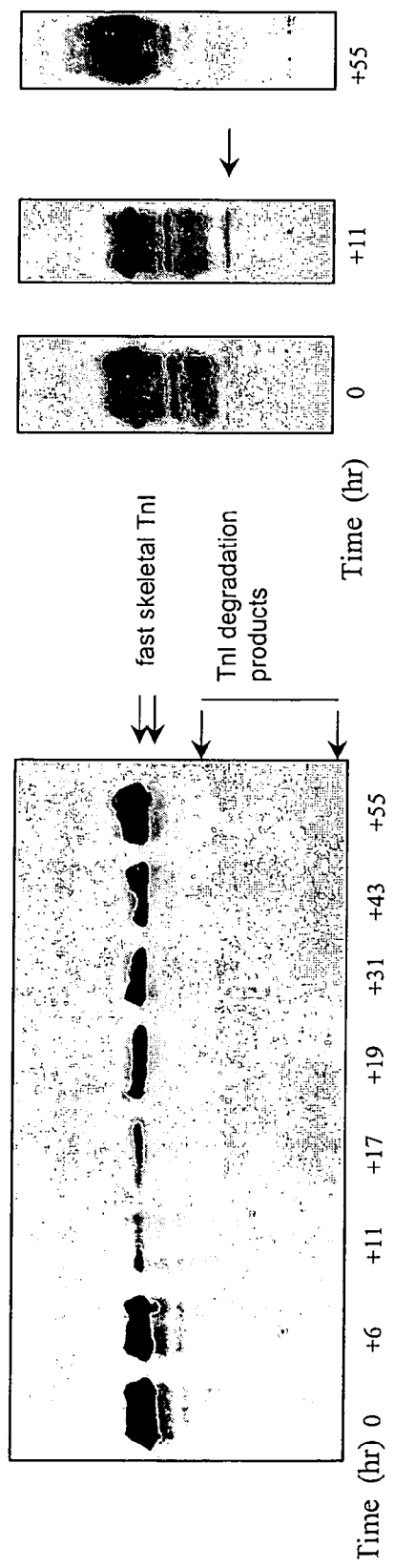
FIG. 9A is a blot wherein the antibody is an anti-skeletal troponin I mAb F-32 (Spectral Diagnostics Inc., Toronto) specific for the fast isoform.
Figure 9B:
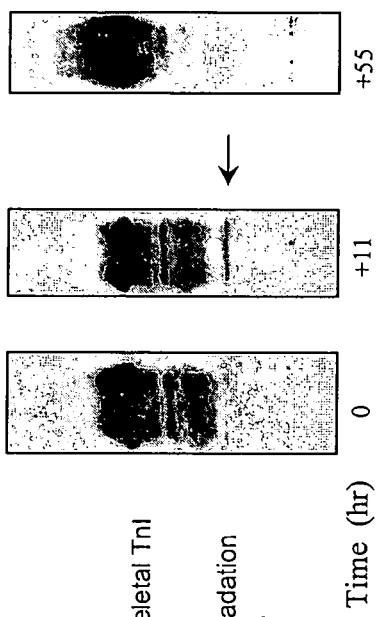
FIG. 9B is a blot show prolonged exposures of three time points from FIG. 9A.
Figure 9C:
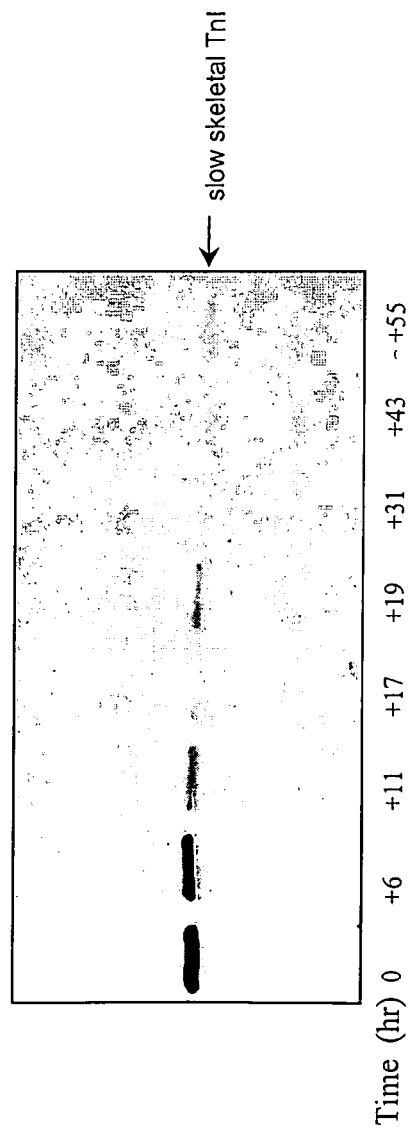
FIG. 9C is a blot wherein the antibody is anti-skeletal troponin I mAb specific for the slow isoform (Matsumoto et al. Biotech. Histochem. 1997 72(4): 191-7). Both the fast and slow isoforms of TnI were detected in this patient.

The methods and kits of the present invention can also be used to monitor damage to skeletal muscle, as well as healing and regeneration of the damaged skeletal muscle. By "damage to skeletal muscle" it is meant to be inclusive of disease, injury and/or fatigue. Examples of skeletal muscle damage which can be diagnosed, monitored and differentially diagnosed from other cell injury via the present invention include, but are not limited to, exercise, traumatic injury including surgery and injury to a limb, muscle wasting during atrophy, sepsis, ischemia, asthma, fatigue, COPD, rhabdomyolosis, and acute respiratory distress syndrome (ARDS). In one embodiment, the ratio of isoforms of a skeletal myofilament protein such as TnI or TnT, are monitored to diagnose and/or assess the severity of a disease involving skeletal muscle. The ratio of two different isoforms of a myofilament protein can also be used to distinguish between different disease types, also referred to herein as differential diagnosis. For example, serum skeletal TnI (skTnI) levels were measured using WB-DSA in two patients with rhabdomyolysis (one patient, FIGS. 7 and 8; a second patient, FIG. 9), and in a patient with the respiratory disorder COPD (FIGS. 7 to 9). The ratio of detectable isoforms of skTnI or shTnT may differ between certain types of skeletal muscle damage as well as during progression and/or healing of the damage as demonstrated in FIGS. 8 and 9. However, with the respiratory condition COPD, only fast TnI was detefcted. Thus, as demonstrated by these experiments, the ratio of the fast form of TnI versus the slow form of TnI can be measured to diagnosis and monitor the state or type of skeletal muscle damage in a subject. Ratios of other isoforms of myofilament proteins which can be measured to diagnosed and monitor the state or type of muscle damage in a subject include, but are not limited to, cardiac troponins versus skeletal troponins, fetal cTnT versus adult cTnT, and ventricle MLC1 versus atrial MLC1.

The invention further provides means to distinguish between different disease types. Referring to FIG. 7, panels A & C are western blots from a respiratory patient, probed respectively with mAb F-32 and mAb 3I-35; panels B & D are similar Western blots from a rhabdomyolysis patient. F-32 detects fast skeletal TnI in both patients, whereas 3I-35 detects this protein only in the respiratory patient. Without being bound by theory, possibly binding of the antibody in this patient is inhibited by a rhabdomyolysis-specific post-translational modification. Alternatively, absence of signal could be indicative of level or severity of disease. Accordingly, differential diagnosis is conveniently provided according to the invention. Such differential diagnosis may also be provided for a variety of other disease states or conditions, potentially exercise, traumatic injury including surgery (e.g., muscle cut during surgery), muscle wasting during atrophy.

The methods and kits of the present invention have also been demonstrated to be useful for early clinical assessment and/or diagnosis of myocardial damage in subjects by detection of low levels of serum myofilament proteins and for monitoring the state of the myocardium in a patient by monitoring myofilament protein levels, preferably myofilament protein modifications, in serum.

By "myocardial damage", for purposes of the present invention, it is meant to be inclusive of any and all types of acute and chronic injury to the heart muscle tissue. Examples of myocardial damage include, but are in no way limited to, damage resulting from early and/or end stage heart failure, hypertension, arteriosclerosis, congestive heart failure, viral attack of the heart muscle, stunning, unstable angina, stable angina, thrombolytic treatment, heart transplant, drug toxicity and sepsis.

For purposes of the present invention, by "early clinical assessment and/or diagnosis" it is meant that myocardial damage is detectable in a patient before the damage results in, causes, or is detectable by ECG and/or where routine clinical testing shows non-significant elevations of biochemical cardiac markers, or when the damage is only minor, such as that resulting from some drug toxicities or sepsis. For purposes of the present invention, by "routine clinical testing" it is meant to be inclusive of commercially available assays such as those for CK-MB, CK, Troponin I (TnI) and Troponin T (TnT).

Using the methods and kits of the present invention, subtle degrees of myocardial damage can be ascertained and monitored by measuring myofilament protein levels in serum of a patient using Western Blot-Direct Serum Analysis (WB-DSA). The sensitivity and specificity of measurement of myofilament proteins in serum by WB-DSA permits detection of myocardial damage very early, even prior to detection of damage by ECG or routine clinical testing showing elevated levels of biochemical cardiac markers. Further, since this method requires denaturation and reduction of proteins, masking or hiding of the epitope of the myofilament protein to be detected by its binding to another protein is not a problem. Increasing the analytical sensitivity (the lowest detectable limit) and specificity for detection of myofilament proteins such as cTnI in serum has implications for earlier detection of cardiac injury associated with acute myocardial infarction, better risk stratification for patients with ACS, and earlier disposition of patients with chest pain of non-cardiac origins. In addition to using this method to monitor the state of the myocardium in patients with suspect AMI or experiencing unstable or stable angina, the increased analytical sensitivity of this method also allows for the development of screening assays to monitor for the presence of myofilament proteins in the serum of patients with coronary artery disease and hypertension, permitting risk stratification and/or customization of treatment strategies. In addition, detecting the presence of myofilament proteins such as cTnI and/or cTnT and/or myosin light chain 1 and/or modification products thereof by the method of the present invention in a patient undergoing anti-thrombolytic therapy is useful in assessing and/or monitoring for clearance of a clot from the coronary arteries.

Examples of antibodies useful in the detection of myofilament proteins in serum via WB-DSA include, but are not limited to, anti-cTnI antibodies such as mAb 8I-7 (amino acid residues 136-154) and 3E3 (residues 1-54, both from Spectral Diagnostics Inc., Toronto, Canada, used at a concentration of 0.5 µg/ml), pAb P1 (residues 1-26, BiosPacific, Emeryville, Calif., 0.5 µg/ml); and mAb 10F2 (residues 188-199, Sanofi Diagnostics Pasteur, Marnes-la-Coquette, France, 0.25 µg/ml); anti-cTnT antibodies such as P1-P3 (BiosPacific, Emeryville, Calif.); JTL-12 (Sigma Chemical Co., St. Louis, Mo.) and 3I-59(Spectral Diagnostics, Toronto, Ontario; Canada); and anti-MLC1 antibodies such as 39-121 (Spectral Diagnostics, Toronto, Ontario Canada). Primary antibody (or antibodies) are detected with a detection means such as horseradish peroxidase (HRP)-conjugated anti-mouse IgG or rabbit anti-goat IgG (both from Jackson Laboratories, West Grove, Pa.) and signals visualized using a calorimetric or chemiluminescence (Boehringer Mannheim) substrate and X-Omat™ Scientific Imaging Film (Eastman Kodak Company, Rochester, N.Y.). All antibodies are diluted in 1% blocking reagent and incubated for 1 hour at room temperature.

Serum cTnI levels were determined using WB-DSA in 10 patients in the emergency department of a teaching hospital complaining of chest pain. In 6 out of 10 cases, cTnI was detected, using Western Blot-Direct Serum Analysis, in the serum of patients presenting with non-diagnostic ECG, where routine clinical testing showed non-significant elevations of biochemical cardiac markers.

Patient 1, a 64-year-old female with a history of coronary artery disease, presented with nausea, retrosternal chest heaviness at rest radiating to both arms, and diaphoresis. The results of her ECG were non-diagnostic, but showed first degree heart block and new ST depression. She was admitted to the cardiology service. Results of biochemical cardiac marker testing by commercially available kits showed CK and CK-MB levels not significantly elevated throughout all time points. Levels of cTnI were detectable by commercially available kits at 15, 22, and 24 hours post-presentation reaching a peak of 0.18 µg/L. Analysis by WB-DSA of serum samples from patient 1 showed cTnI absent at time of presentation, but clearly present at one hour after admission and remaining detectable 24 hours post-presentation. This patient was discharged from the hospital with a diagnosis of second degree heart block.

Patient 2 was a 73-year-old male, with a family history of cardiovascular disease, who had experienced a myocardial infarction within the last six months. He presented to emergency with chest pain of 1.5 hours duration, but with no other associated cardiac symptoms. The results of his ECG showed inferior-lateral T wave inversion with inferior Q waves. CK, CK-MB, and cTnI values determined by commercially available kits were not significantly elevated. Analysis of serum samples by WB-DSA from patient 2 showed cTnI to be present at admission and to remain detectable throughout, until the last sample was taken 21 hours later. This patient was discharged from the hospital with the diagnosis of unstable angina.

Patient 3, a 47-year-old male with hypertension and coronary artery disease, presented with retrosternal tightness radiating down his left arm, and no other associated cardiac symptoms. The ECG was non-diagnostic, showing no acute changes from past ECGs. Routine clinical testing by commercially available kits showed CK and CK-MB levels that were not significantly elevated. cTnI measured using a commercially available kit appeared elevated (borderline) at one and four hours post-presentation at 0.2 µg/L and 0.6 µg/L, respectively. WB-DSA showed cTnI present at admission and at all subsequent time points analyzed. Patient 3 was discharged from hospital with the diagnosis of unstable angina.

Patient 4, an 80-year-old female with hypertension and a history of angina, presented with a pattern of chest pain recognized as unstable angina. Results of her ECG showed a new left bundle branch block. CK and CK-MB levels determined using commercially available kits were elevated in this patient, but did not change significantly throughout her hospital admission and this level of elevation had been present on previous admissions cTnI levels determined using commercially available kits were negative. Serum analysis by WB-DSA showed cTnI present at admission, with the signal tapering off by the sixth hour after admission. This patient was discharged from hospital with the diagnosis of unstable angina.

Patient 5, a 69-year-old female with no previous history of cardiac illness, presented with central chest pain radiating to her left shoulder. ECG results showed T wave flattening in anterior leads, but were otherwise normal. Results from routine clinical testing using commercially available kits showed that CK, CK-MB, and cTnI levels did not change significantly throughout her assessment. Analysis by WB-DSA of serum samples obtained from this patient showed cTnI to be present at admission, with the signal increasing thereafter at all subsequent time points. Patient 5 was discharged from the emergency department with the diagnosis of chest pain/not yet diagnosed. This patient revisited the emergency department 2 months later complaining of chest pain.

Patient 6, a 73-year-old female with hypertension and congestive heart failure, presented with weakness and chest pain that radiated to the back. The results of her ECG were non-diagnostic, showing a sinus rhythm with a left bundle branch block and no new changes. CK, CK-MB, and cTnI levels determined using commercially available kits were not significantly elevated throughout her assessment. WB-DSA showed cTnI absent at admission, a faint signal present at 1 hour after admission, but clearly present at 2 and 4 hours after admission. This patient was discharged from the emergency department with the diagnosis chest pain/not yet diagnosed.

Serum samples from four additional patients (patients 7-10) with non-significant elevations in biochemical cardiac markers determined using commercially available kits, and discharged with the diagnosis of angina (n=3) or chest pain/not yet diagnosed (n=1), were analyzed by WB-DSA. The results of WB-DSA showed that no cTnI was present in their serum.

Results from these patients demonstrate the superior analytical sensitivity, compared to routine clinical tests, of WB-DSA in the detection of myofilament proteins such as cTnI (and its modification products) in the serum of patients presenting with symptoms of ACS. As shown herein, this method allowed for earlier detection of a myofilament protein, in this example cTnI, in serum of patients with symptoms of ACS, compared to routine clinical tests. In addition, in some patients demonstrating non-significant elevations in biochemical cardiac markers measured by commercially available kits and a non-diagnostic ECG, WB-DSA was capable of detecting this myofilament protein in serum. In fact, 50% (⅜) of the patients in which cTnI was detected only by WB-DSA revisited the emergency department 2-3 months later with complaints of chest pain. Considering that the prognosis of patients with elevated cTnI levels is negatively related to the degree of cTnI elevation (Morrow et al. Clin. Chem. 2000 46(4):453-460), the method of the present invention is believed to provide a better diagnostic tool for myocardial damage and provides improved risk stratification.

Figure 6:
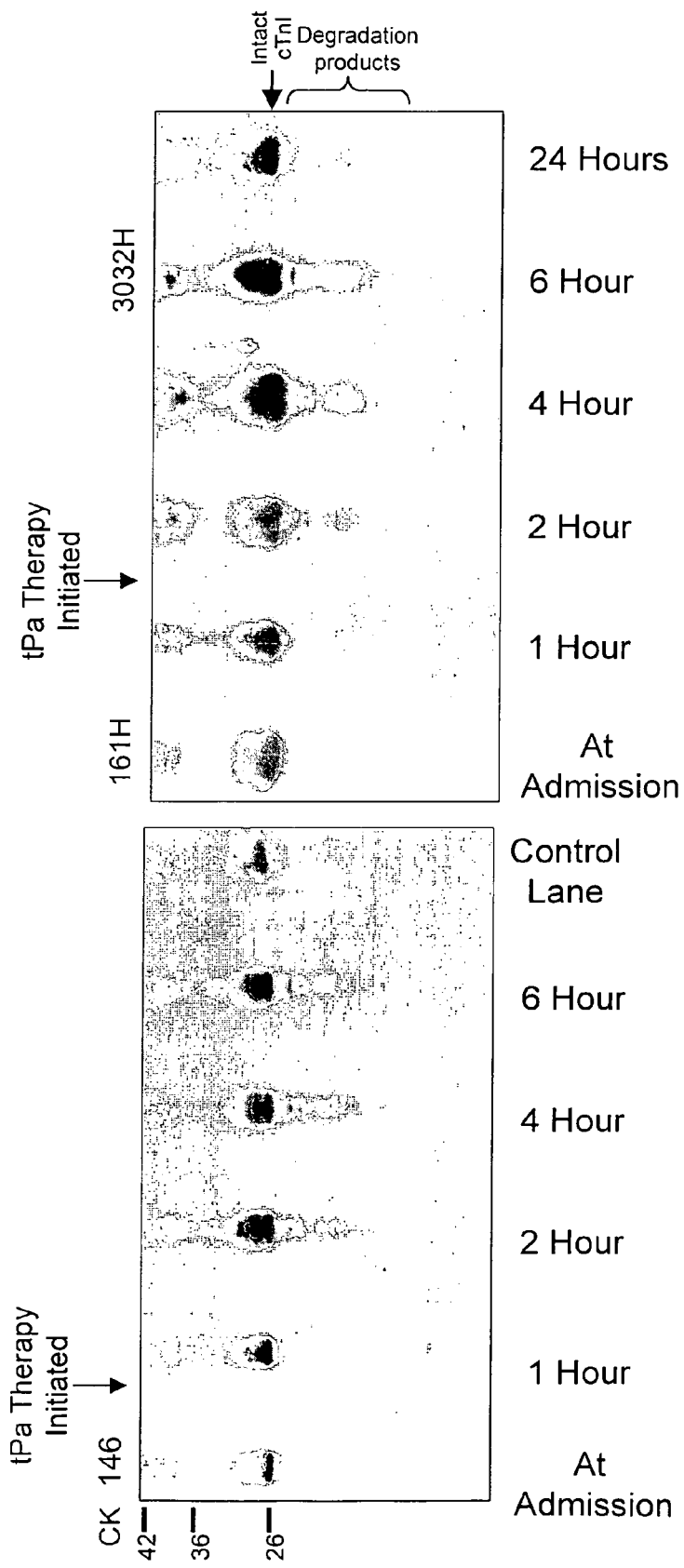
FIG. 6 provides a western blot from serum analyzed by WB-DSA from a patient undergoing thrombolytic therapy (TPA) for a blocked coronary artery. Only intact cTnI was observed in the patient's serum prior to treatment. Upon reperfusion, however, degradation products were also observed.
Figure 7A:
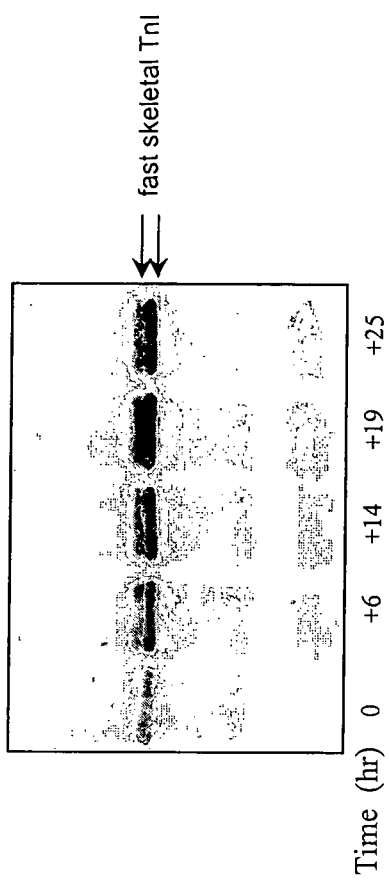
FIG. 7 provides a western blot from serum analyzed by WB-DSA of serial time points (initial sample time point designated time zero) of a patient with the respiratory muscle dysfunction chronic obstructive pulmonary disorder (COPD) (FIG. 7A and FIG. 7C) and a patient with rhabdomyolysis (FIG. 7B and FIG. 7D). Using MAbs 3I-35 (specific for all isoforms of troponin I (fast, slow, and cardiac) and F-32 (specific for fast skeletal troponin I) (both from Spectral Diagnostics Inc., Toronto)), skeletal troponin I (skTnI) was detected in serum at all time points in the patient with COPD and the patient with rhabdomyolysis, respectively. However, mAb F-32 did not reveal skTnI in the first time point of the patient with COPD (FIG. 7A) and mAb 3I-35 did not reveal skTnI in any time point of the patient with rhabdomyolysis (FIG. 7D). Blots depicted in FIGS. 7A and 7D were prepared using longer exposures (overnight versus 1 hour) than those depicted in FIGS. 7B and 7C, to increase the ability to detect any cTnI. The blot depicted in FIG. 7D shows cross reactivity with IgG.
Figure 7C:
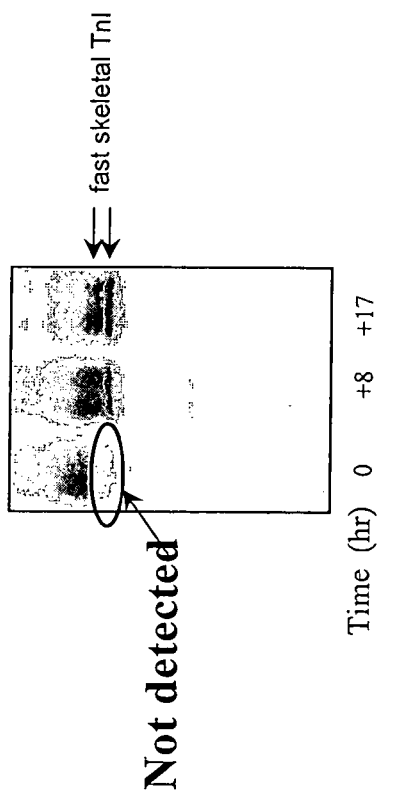
Figure 7B:
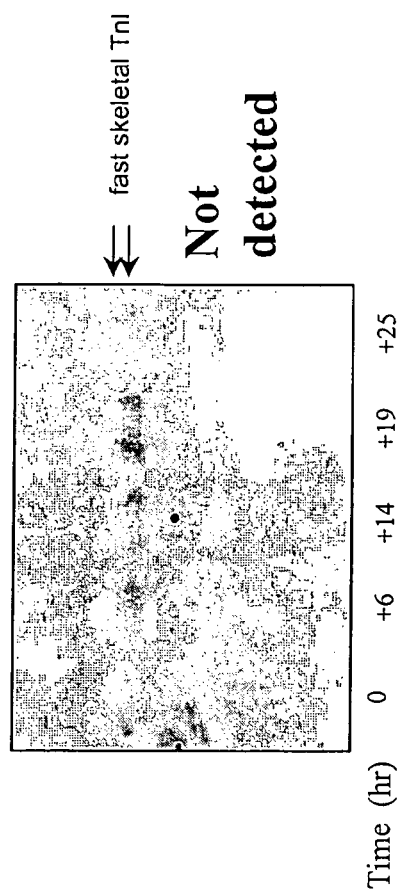
Figure 7D:
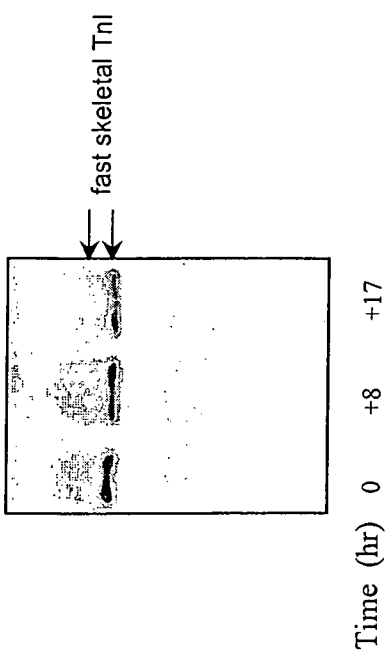
Figure 8A:
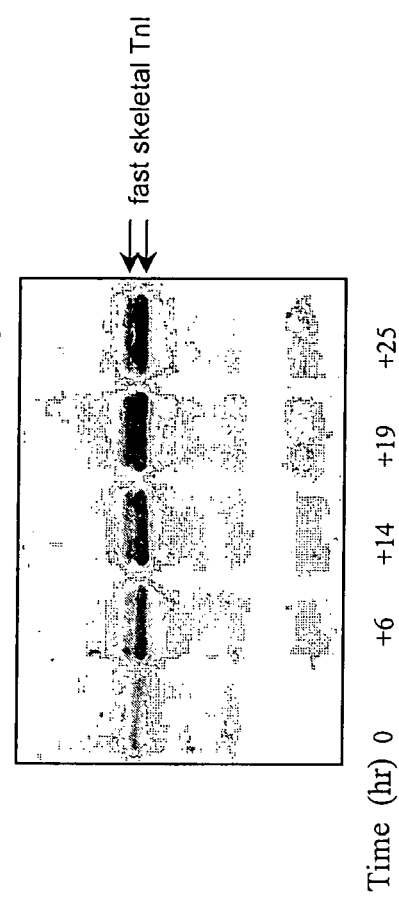
FIG. 8 provides a western blot of serum analyzed by WB-DSA of serial time points (initial sample time point designated time zero) of a patient with respiratory muscle dysfunction (COPD) (FIGS. 8A and 8C) and a patient with rhabdomyolysis (FIGS. 8B and 8D). Blots depicted in FIGS. 8A and 8B were prepared with mAb F-32 specific for the fast isoform of skTnI (Spectral Diagnostics Inc., Toronto); blots depicted in FIGS. 8C and 8D were prepared with a mAb specific for the slow isoform of skTnI (Matsumoto et al. Biotech. Histochem. 1997 72(4):191-7). The fast, but not the slow, isoform of skTnI was detected in the patient with COPD while both isoforms were detected in the patient with rhabdomyolysis.
Figure 8C:
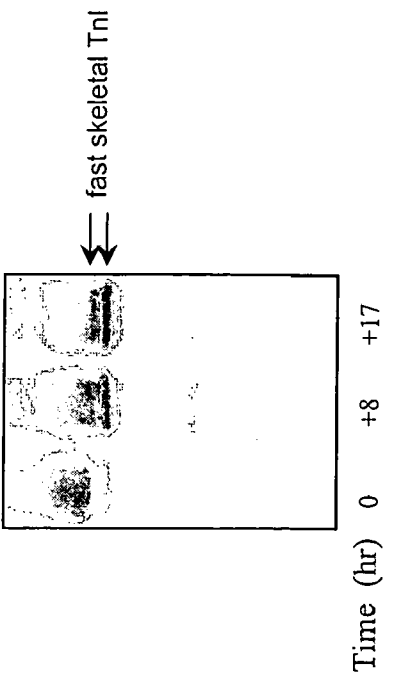
Figure 8B:
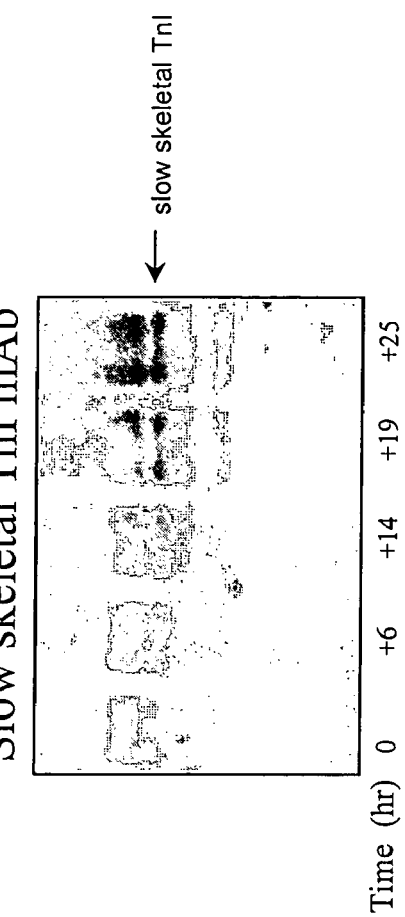
Figure 8D:
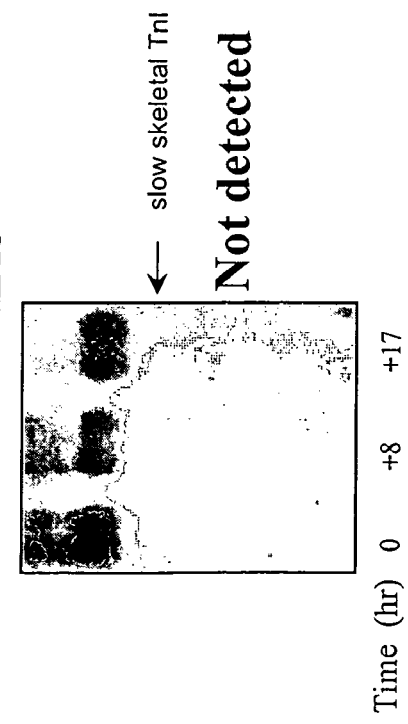

Interestingly, only intact cTnI, and not degradation products, was observed in this cohort of patients with non-significant elevation of biochemical cardiac markers and non-diagnostic ECG. This finding, which reflects subtle myocardial damage, is in sharp contrast to observations discussed supra of multiple cTnI degradation products in serum in patients diagnosed with acute myocardial infarction, as assessed by WB-DSA. A patient undergoing thrombolytic therapy (TPA) for a blocked coronary artery also had only intact cTnI in his serum prior to treatment. Upon reperfusion, however, degradation products were also observed. See FIG. 6. These results reflect the subtle myocardial injuries observable in patients with conditions across the spectrum of ACS using WB-DSA, in comparison to patients having already suffered an acute myocardial infarction.

Since ACS represents a spectrum of cardiac pathophysiology, unique patterns of myofilament protein modifications may also be detectable in serum using WB-DSA at various points along this spectrum. For example, it is believed that the status of cTnI and/or cTnT and their patterns of modifications in serum reflect the state of the myocardium, since cTnI and/or cTnT can be modified in the myocardium prior to release into the circulation. Accordingly, the method for monitoring the state of the myocardium of a patient by monitoring degradation of myofilament proteins such as cTnI and/or cTnT in their serum by WB-DSA is also provided by the present invention.

The experiments described herein have focused upon use of the method of the present invention to detect, diagnose and monitor damage in muscle cells. However, as will be understood by one of skill in the art upon reading this disclosure, the method is also applicable to detecting, diagnosing and monitoring damage to other cells including, but not limited to, kidney, liver, brain, gastrointestinal, and vascular cells.

The following nonlimiting examples are provided to further illustrate the present invention.

EXAMPLES

Example 1

Muscle Damage Assessment

Patient Sampling

Blood samples from 12 patients admitted to a hospital emergency department, with chest pain and unequivocal signs of AMI (based upon electrocardiographic findings) were obtained. Serum sampling was performed according to routine care protocols and not by a defined study time course. This led to different intervals between successive blood samples, thus permitting study of the occurrence of biochemical markers in a "real-life" scenario.

Routine Biochemical Testing

Blood was collected in serum separator tubes, centrifuged and assayed immediately for routine biochemistry tests. Samples were then frozen until WB-DSA. Routine testing included total creatine kinase (CK, measured by CX7, Beckman Coulter, Inc., Fullerton, Calif.), its MB isoenzyme (CKMB) and cTnI (both measured by Technicon Immunol, Bayer Corporation, Tarrytown, N.Y.). A diagnosis of AMI was confirmed if there was a typical time profile observed for CK with at least a doubling from baseline values. Confirmatory testing by either CKMB or cTnI was also required on at least one sample. CKMB was considered positive if the absolute value was above 8 μg/L and the relative index (CKMB*100/CK) was above 3%. cTnI was considered positive above 0.9 μg/L.

Stability Studies for cTnI and cTnT

To determine the proteolytic susceptibility of cTnI and cTnT in serum, full length human recombinant cardiac TnI (209 amino acids), human recombinant cardiac TnI amino acid fragment 1-192, and human recombinant cardiac TnT (rcTnI, rcTnI$_{1-192}$ and rcTnT) were added to 3 separate serum pools at a final concentration of 100 μg/L and incubated at 37° C. for up to 48 hours. The serum was obtained from a 28-year-old healthy male volunteer (and hereafter referred to as normal serum).

Electrophoresis and Western Blot Analysis

Polyacrylamide gel electrophoresis was performed under denaturing and reducing conditions using a sample buffer containing 0.33% SDS, 0.33% CHAPS, 0.33% NP-40, 0.1 M DTT, 4 M urea, and 50 mM Tris-HCl, pH 6.8 in 50% glycerol. Serum was diluted 12.5-times in sample buffer to prevent precipitation of serum proteins during boiling. Diluted samples were then boiled for 10 minutes, to assure separation of the troponins from serum proteins and to break-up binary and ternary complexes. Twenty-five μl (equivalent to 2 μl of neat serum) were then loaded on 12% gels (14 cm×14 cm×0.75 mm), which were run at 110 V for 5 hours. After gel electrophoresis proteins were transferred onto nitrocellulose (45 Micron, Micton Separation Inc., Westborough, Mass.) in 10 mM CAPS, pH 11.0 for 1 hour at 100 V and 4° C. Thereafter, membranes were blocked over night at 4° C. in 10% blocking reagent (Boehringer Mannheim, Mannheim, Germany). Western blot analysis was then carried out with the following anti-cTnI antibodies (with epitopes to): mAb 8I-7 (amino acid residues 136-154) or 3E3 (residues 1-54, both from Spectral Diagnostics Inc., Toronto, Canada, used at a concentration of 0.5 μg/ml); pAb P1 (residues 1-26, BiosPacific, Emeryville, Calif., 0.5 μg/ml); mAb 10F2 (residues 188-199, Sanofi Diagnostics Pasteur, Marnes-la-Coquette, France, 0.25 μg/ml). cTnT was probed with pAb anti-cTnT (residues 3-15, BiosPacific, Emeryville, Calif., 0.5 μg/ml), detecting all isoforms of cTnT. Primary antibodies were detected with horseradish peroxidase (HRP)-conjugated goat anti-mouse IgG or rabbit anti-goat IgG (both from Jackson Laboratories, West Grove, Pa.) and signals visualized using chemiluminescence substrate (Boehringer Mannheim) and X-Omat™ Scientific Imaging Film (Eastman Kodak Company, Rochester, N.Y.). All antibodies were diluted in 1% blocking reagent and incubated for 1 hour at room temperature.

Dephosphorylation of Serum

Based on previously published protocols (Swarup et al. J Biol Chem. 1981 256:8197-8201; Shenolikar, S. and Ingebritsen, T. S. Protein (serine and threonine) phosphate phosphatases. In: Wold F, Moldave K, editors. Methods in enzymology. vol. 107. London: Academic Press; 1984. p. 102-129) dephosphorylation of serum has been performed as follows: one hundred units of calf intestinal alkaline phosphatase (AP, New England Biolabs, Beverly, Mass.) and 1.6 μl of 10× dephosphorylation buffer (50 mM Tris, 100 mM NaCl, 10 mM MgCl$_2$, 1 mM DTT pH 7.9) were added to 4 μl of serum (approx. 100 mg/ml serum proteins) and incubated for 30 minutes at 30° C. (1 unit of AP hydrolyses 1 nmole of p-nitrophenylphosphate/minute at 30° C. and pH 8.5). Reactions were terminated by addition of 4 μl of 5× sample buffer and boiling for 5 minutes. The activity of AP in serum was confirmed by its ability to dephosphorylate $^{32}$P-labeled myelin basic protein when added to normal serum.

Example 2

Diagnosing Cardiac Muscle Damage

Patient Samples

Serum samples were obtained from a prospective case series of patients presenting, within four hours onset of symptoms of ACS, to a hospital emergency department. Serum samples of ten representative cases were selected from the first 45 cases of ACS enrolled, who also had non-diagnostic ECG and non-significant elevations in the biochemical cardiac markers CK, CK-MB, and cTnI using commercially available kits. Patients underwent a history and clinical examination, a 12 lead ECG was recorded and serial blood was drawn at presentation, and subsequently at 1, 2, 4, 6 and 16-24 hours for routine clinical testing of biochemical cardiac markers and for analysis by WB-DSA. Serum samples were stored at −80° C. until analyzed. Final discharge diagnosis from the emergency department was based on standard criteria of history, physical examination, ECG changes, and biochemical cardiac markers.

Analytical Biochemical Testing

Total CK levels were assayed using the Synchron CX7 (Beckman Instruments, Brea, Calif.). MB isoenzyme and cTnI were assayed using the Technicon Immuno I (Bayer Corporation, Tarrytown, N.Y.). The reference range for CK was 55 to 197 U/L for men and 35 to 155 U/L for women. The precision of the CX7 for CK at concentrations of 131 and 480 U/L was reflected by coefficient of variations (CV %) of 2.9 and 2.65%, respectively. The precision of the Technicon Immuno I for cTnI at concentrations of 3 and 27 μg/L is reflected in CV % of 3.2 and 2.9%, respectively. A 20% elevation in CK values was considered to be a significant increase. Testing for the CK-MB fraction was considered negative if the concentration was <8 μg/L and positive if the concentration was >8 μg/L, with a relative index (CK-MB×100/CK) greater than 3%. For cTnI, the minimum detectable concentration reported for Immuno 1 is 0.1 μg/L.

Western Blot-Direct Serum Analysis

Two microliters of serum was diluted 12.5× in sample buffer consisting of 0.33% (w/v) SDS, 0.33% (w/v) CHAPS, 0.33% (w/v) NP-40, 0.1 M dithiothreitol, 1 M urea, and 50 mM/L Tris-HCl (pH 6.8) in 50% glycerol. Proteins were resolved by SDS-PAGE (12%) and transferred to nitrocellulose. Western blot analysis was performed using the following anti-cTnI antibodies: Mab 8I-7 (epitope amino acid 136-154 (Spectral Diagnostics, Toronto, Canada), which can detect the majority of forms of cTnI, both proteolyzed and modified (McDonough et al. Circ. Res. 1999 84:9-20; McDonough et al. Circ. 2001 103:58-64), and polyclonal antibody P3 (epitope amino acid 26-58) (BiosPacific, Emeryville, Calif.). Additional samples from healthy individuals (n=6) and from a patient diagnosed as asthmatic (chest pain of noncardiac origin) were analyzed as negative controls. No cTnI was detected in any of these samples. For comparison (control analysis), serum from a healthy individual was spiked with human recombinant intact cTnI1-200 and cTnI1-209 (the primary cTnI degradation product observed in stunned myocardium from isolated hearts) (McDonough et al. Circ. Res. 1999 84:9-20; Gao et al. Circ. Res. 1997 80:393-399; Van Eyk et al. Circ. Res. 1998 82:261-271) and resolved alongside each patient's samples. Serum from each patient was also resolved and probed with only secondary antibody to control for cross reactivity with the patients' IgG.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of diagnosing, monitoring, or differentially diagnosing muscle damage in a subject, comprising characterizing two or more isoforms of a myofilament protein, or a modification product thereof, in a biological sample obtained from the subject, wherein the myofilament protein is troponin T.

2. The method of claim 1, wherein characterizing comprises at least one of quantifying, obtaining a profile, determining a ratio, determining relative level, and determining presence or absence of the two or more isoforms of a myofilament protein.

3. The method of claim 1, wherein the proteins are separated and characterized by Western blot.

4. The method of claim 1, wherein the biological sample comprises at least one of serum, plasma, urine, amniotic fluid, lymph, and cerebrospinal fluid.

5. The method of claim 1, wherein the biological sample comprises serum.

6. A method of diagnosing, monitoring, or differentially diagnosing muscle damage in a subject, comprising characterizing at least two isoforms of one myofilament protein, or modification products thereof, and at least two isoforms of another myofilament protein, or modification products thereof, in a biological sample obtained from the subject, wherein the myofilament proteins are selected from myosin light chain 1, troponin I, troponin T, and troponin C.

7. The method of claim 6, wherein one said myofilament protein is troponin I.

8. The method of claim 6, wherein the myofilament proteins are troponin I and troponin T.

9. A method of diagnosing, monitoring, or differentially diagnosing skeletal muscle damage in a subject, comprising characterizing two or more isoforms of a skeletal myofilament protein, or a modification product thereof, in a biological sample obtained from the subject, wherein the skeletal myofilament protein is a troponin.

10. The method of claim 9, wherein the skeletal myofilament protein is troponin I.

11. The method of claim 10, wherein the two isoforms of the skeletal myofilament protein are slow skeletal troponin I and fast skeletal troponin I.

12. The method of claim 9, wherein the skeletal myofilament protein is troponin T.

13. The method of claim 12, wherein the two isoforms of the skeletal myofilament protein are slow skeletal troponin T and fast skeletal troponin T.

14. The method of claim 9, further comprising following the progression of muscle damage by characterizing two or more isoforms of a myofilament protein, or modification products thereof, at two or more times.

15. The method of claim 9, wherein the skeletal muscle damage is associated with at least one of exercise, trauma, surgery, atrophy, sepsis, ischemia, asthma, fatigue, drug toxicity, chronic obstructive pulmonary disorder (COPD), rhabdomyolysis, respiratory disease, and acute respiratory distress syndrome (ARDS).

16. The method of claim 9, wherein characterizing comprises at least one of quantifying, obtaining a profile, determining a ratio, determining relative level, and determining presence or absence of the two or more isoforms of a myofilament protein.

17. The method of claim 9, wherein the biological sample comprises at least one of serum, plasma, urine, amniotic fluid, lymph, and cerebrospinal fluid.

18. The method of claim 9, wherein the biological sample comprises serum.

19. A method of diagnosing, monitoring, or differentially diagnosing muscle damage in a subject, comprising characterizing cardiac and slow skeletal isoforms of a troponin, or modification products thereof, in a biological sample obtained from the subject.

20. The method of claim 19, wherein the cardiac and slow skeletal isoforms of a troponin are selected from troponin I, troponin T, troponin C, and a combination thereof.

21. The method of claim 19, further comprising following progression of muscle damage by characterizing cardiac troponin isoforms and skeletal troponin isoforms at two or more times.

22. The method of claim 19, wherein the muscle damage is at least one of skeletal muscle damage and cardiac muscle damage.

23. The method of claim 19, wherein the muscle damage is associated with at least one of exercise, trauma, surgery, atrophy, sepsis, ischemia, asthma, fatigue, chronic obstructive pulmonary disorder (COPD), rhabdomyolysis, acute respiratory distress syndrome (ARDS), heart failure, hypertension, arteriosclerosis, viral attack of heart muscle, stunning, angina, thrombolytic treatment, heart transplant, and drug toxicity.

24. A method of diagnosing, monitoring, or differentially diagnosing muscle damage in a subject, comprising characterizing a cardiac troponin and
   (a) fast skeletal troponin C;
   (b) fast skeletal troponin T; or
   (c) two or more of fast skeletal troponin I, fast skeletal troponin C, and fast skeletal troponin T; or modification products thereof, in a biological sample obtained from the subject.

25. The method of claim 24, wherein the cardiac troponin is selected from troponin I, troponin T, troponin C, and a combination thereof.

26. The method of claim 24, further comprising following progression of muscle damage by characterizing cardiac troponin isoforms and skeletal troponin isoforms at two or more times.

27. The method of claim 24, wherein the muscle damage is at least one of skeletal muscle damage and cardiac muscle damage.

28. A method of diagnosing, monitoring, or differentially diagnosing muscle damage in a subject, comprising characterizing cardiac, slow skeletal, and fast skeletal isoforms of a troponin, or modification products thereof, in a biological sample obtained from the subject.

29. The method of claim 28, wherein the cardiac, slow skeletal, and fast skeletal isoforms of a troponin are selected from troponin I, troponin T, troponin C, and a combination thereof.

30. A method of diagnosing, monitoring, or differentially diagnosing cardiac muscle damage in a subject, comprising characterizing two or more isoforms of a cardiac myofilament protein, or modification products thereof, in a biological sample obtained from the subject, wherein the cardiac myofilament protein is a troponin.

31. The method of claim 30, further comprising following progression of cardiac muscle damage by characterizing two or more isoforms of a cardiac myofilament protein at two or more times.

32. A method of diagnosing, monitoring, or differentially diagnosing cardiac muscle damage in a subject, comprising characterizing two or more isoforms of a cardiac myofilament protein, or modification products thereof, in a biological sample obtained from the subject, wherein the two isoforms are ventricular myosin light chain 1 and atrial myosin light chain 1.

33. The method of claim 32, further comprising following progression of cardiac muscle damage by characterizing two or more isoforms of a cardiac myofilament protein at two or more times.

* * * * *